US011090010B2

(12) United States Patent
Nishiyama et al.

(10) Patent No.: US 11,090,010 B2
(45) Date of Patent: Aug. 17, 2021

(54) INFORMATION PROVIDING METHOD, INFORMATION PROCESSING SYSTEM, INFORMATION TERMINAL, AND INFORMATION PROCESSING METHOD

(71) Applicant: Panasonic Intellectual Property Management Co., Ltd., Osaka (JP)

(72) Inventors: Yukari Nishiyama, Tokyo (JP); Masahiko Tsukuda, Osaka (JP); Yasuaki Okumura, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 202 days.

(21) Appl. No.: 16/586,833

(22) Filed: Sep. 27, 2019

(65) Prior Publication Data
US 2020/0022661 A1    Jan. 23, 2020

Related U.S. Application Data

(63) Continuation of application No. PCT/JP2018/021455, filed on Jun. 5, 2018.

(30) Foreign Application Priority Data

Jul. 7, 2017  (JP) .............................. JP2017-133354

(51) Int. Cl.
    *A61B 5/00* (2006.01)
(52) U.S. Cl.
    CPC .......... *A61B 5/7296* (2013.01); *A61B 5/0004* (2013.01); *A61B 5/0022* (2013.01); *A61B 5/4343* (2013.01); *A61B 5/6824* (2013.01)

(58) Field of Classification Search
    CPC ............ A61B 2503/02; A61B 2503/04; A61B 2560/0214; A61B 5/0004; A61B 5/0022;
    (Continued)

(56) References Cited

U.S. PATENT DOCUMENTS

2014/0288401 A1   9/2014  Ouwerkerk et al.
2016/0058376 A1   3/2016  Baek et al.

FOREIGN PATENT DOCUMENTS

JP         2014-191467         10/2014

OTHER PUBLICATIONS

International Search Report of PCT application No. PCT/JP2018/021455 dated Aug. 28, 2018.
(Continued)

*Primary Examiner* — Jonathan T Kuo
(74) *Attorney, Agent, or Firm* — Greenblum & Bernstein, P.L.C.

(57) ABSTRACT

A method comprising: acquiring via a network biogas information representing a concentration of furfural of the user acquired by a sensor that detects the furfural discharged from a skin surface of the user; obtaining the reference information representing a lower limit of a normal range of the concentration of furfural per unit period of time, using a memory storing the reference information; and outputting information related to stress of the user an information terminal of the user, after it is determined that a frequency that concentration of the furfural of the user per the unit period of time is less than the lower limit of the normal range tends to increase, based on the biogas information acquired in a pregnancy period of the user.

18 Claims, 18 Drawing Sheets

(58) Field of Classification Search
CPC ... A61B 5/14546; A61B 5/165; A61B 5/4266; A61B 5/4277; A61B 5/4343; A61B 5/6824; A61B 5/6831; A61B 5/6832; A61B 5/7275; A61B 5/7296; G01N 33/497; G06Q 50/22; G16H 40/67; G16H 50/30

See application file for complete search history.

(56) References Cited

OTHER PUBLICATIONS

Japanese Cabinet Office, "White Paper on National Life (2008)", Chapter 1, Section 3, "2. Stressful Society and Modern pathology", Dec. 26, 2008 (Whole Sentence Translation).

General Conference (2013), Special Lectures, "Grasping Metal Problems of Pregnant Woman and Child Care", Keiko Yoshida, Child Health in Okinawa, vol. 41 (2014), Mar. 2014, pp. 3-8 (Whole Sentence Translation).

The Extended European Search Report dated Jun. 3, 2020 for the related European Patent Application No. 18828153.9.

FIG. 4

|  | DURING STRESS TASK | DURING RELAXATION TASK |
|---|---|---|
| No. 1 | 0.98 | 1 |
| No. 2 | 0.91 | 1 |
| No. 3 | 0.90 | 1 |
| No. 4 | 0.99 | 1 |
| No. 5 | 1.05 | 1 |
| No. 6 | 0.84 | 1 |
| No. 7 | 0.75 | 1 |
| No. 8 | 0.94 | 1 |
| No. 9 | 0.63 | 1 |
| No. 10 | 1.12 | 1 |
| No. 11 | 0.22 | 1 |
| No. 12 | 2.10 | 1 |
| No. 13 | 0.96 | 1 |
| No. 14 | 1.21 | 1 |
| No. 15 | 0.88 | 1 |
| No. 16 | 0.80 | 1 |
| No. 17 | 0.83 | 1 |
| No. 18 | 0.91 | 1 |
| No. 19 | 0.56 | 1 |
| No. 20 | 0.75 | 1 |
| AVERAGE | 0.92 | 1 |

INFORMATION PROVIDING METHOD, INFORMATION PROCESSING SYSTEM, INFORMATION TERMINAL, AND INFORMATION PROCESSING METHOD

TECHNICAL FIELD

The present disclosure relates to an information providing method and the like.

BACKGROUND ART

PTL 1 discloses a maternal and child health handbook electronic system that provides information by analyzing contents of items described in a maternal and child health handbook and notifying local government service contents desired by a user or suitable for the user.

In Japan, a maternal and child health handbook is issued to a pregnant woman from a local government when pregnancy is found. The pregnant woman, a medical institution, and the local government fill in the maternal and child health handbook with information related to health conditions of the pregnant woman until childbirth, and health conditions of a child during and after the childbirth, a record of immunization of the child, a growth state of the child, and the like. Maternal and child health handbooks each serve to store a growth record of a child. While the maternal and child health handbooks are each a paper medium, a system of electronizing the maternal and child health handbooks also has been studied.

The system of PTL 1 extracts information on a pregnant woman, or information on a child, from a database of electronize maternal and child health handbooks, and compares the information with a reference value that is preliminarily registered. The information on a pregnant woman includes a user ID, a user name, a name of a child, information on the pregnant woman, information on the child, questionnaires, and details of consultation. For example, when a child of one year old has a weight that is out of the infant's growth curve, information on the child is determined to be out of a reference value. Then, alert information indicating that the child may have a problem in health conditions, as well as recommended information recommending an interview with a hygienist, is notified to a user terminal. As a result, depression, child abuse, and the like are prevented.

CITATION LIST

Patent Literature

PTL 1: Japanese Patent Application Publication No. 2014-191467

SUMMARY OF THE INVENTION

Technical Problem

Unfortunately, the conventional art described above is required to be further improved.

Solution to Problem

An aspect of the invention according to the present disclosure is a method for providing information in an information processing system, the method comprising:

acquiring, via a network, biogas information representing a concentration of furfural of a user acquired by a sensor that detects the furfural discharged from a skin surface of the user;

obtaining reference information representing a lower limit of a normal range of the concentration of furfural per unit period of time, using a memory storing the reference information representing the lower limit of the normal range; and outputting information related to stress of the user to an information terminal after it is determined that a frequency with which the concentration of the furfural of the user per unit period of time is less than the lower limit of the normal range tends to increase, based on the biogas information acquired in a pregnancy period of the user.

Advantageous Effect of Invention

According to the above aspect, further improvement can be achieved.

BRIEF DESCRIPTION OF DRAWINGS

FIG. 4 is a list showing relative values of peak areas of furfural in mass spectrum data acquired when biogas collected from a hand of each of test subjects during the stress task is analyzed with a gas chromatography-mass spectrometry (GC/MS) by assigning 1 to a peak area of furfural in mass spectrum data acquired when biogas collected from the hand of each of the test subjects during the relaxation task is analyzed by the GC/MS.

DESCRIPTION OF EMBODIMENTS

Figure 1:
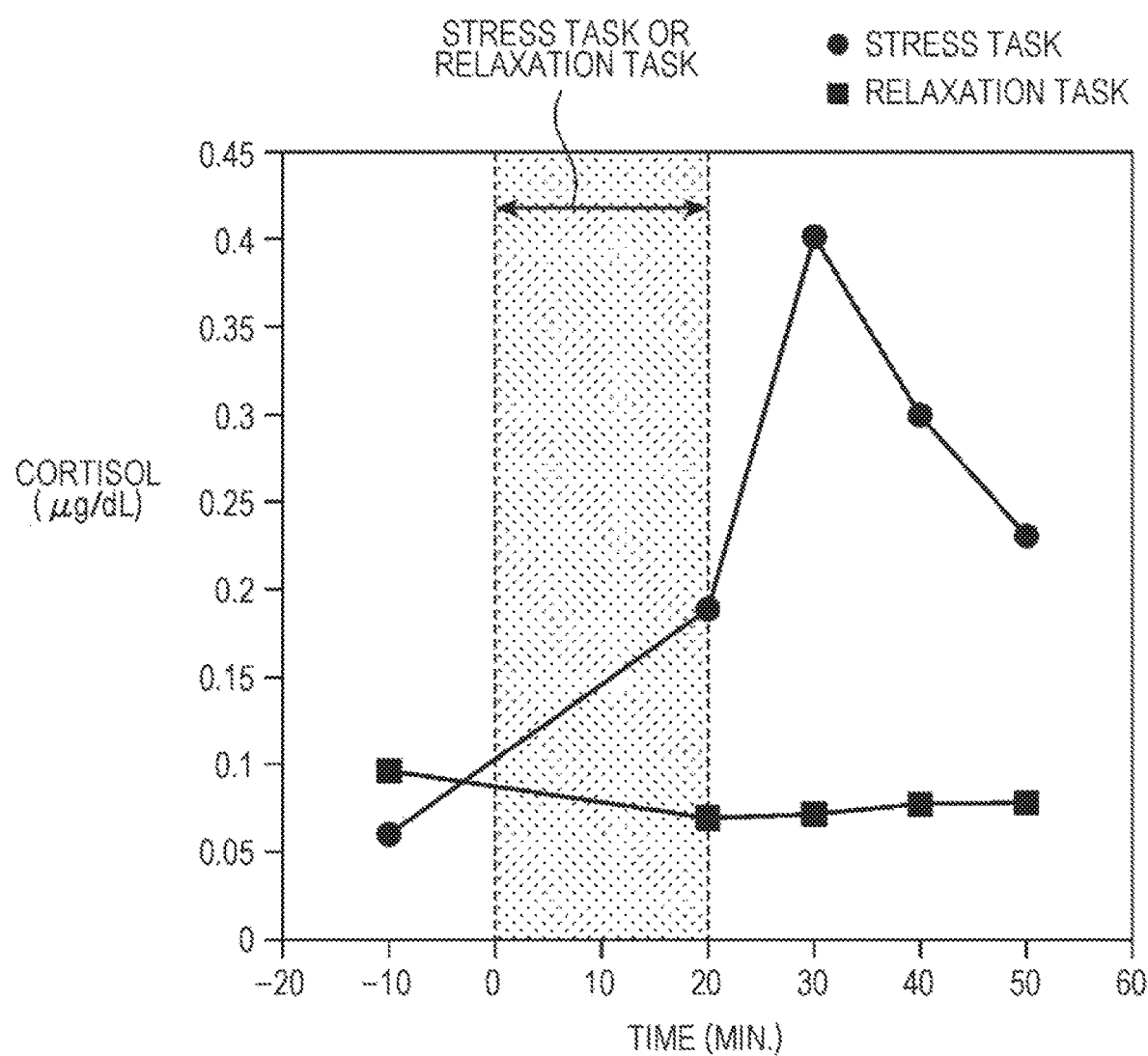
FIG. 1 is a graph showing temporal change in concentration of cortisol in saliva of a test subject before and after a stress task, and before and after a relaxation task.

Reason for Inventing an Aspect According to the Present Disclosure

First, a viewpoint of an aspect according to the present disclosure will be described.

The present inventors research prevention of postpartum depression.

That is, while treatment of postpartum depression is entrusted to a psychiatrist when it appears, they have researched prevention of postpartum depression by grasping a sign of the postpartum depression before it appears.

The present inventors set a hypothesis that there is a kind of cause and effect relationship between stress and depression. That is, stress is not necessarily harmful for mind and body. However, accumulation of stress tends to have adverse effects on mind and body, so that it is conceivable that the adverse effects include depression.

Depression is classified into three causes such as (1) "physical", (2) "endogenous", and (3) "psychogenesis", The "physical" depression is caused by a characteristic of a brain or a bodily organ, or a medication. The "endogenous" depression is caused by a variation at a gene level, or by a factor causing mental disorder, naturally being included in a brain. The "psychogenesis" depression is caused by experience of psychological stress. It is difficult to strictly classify depression into these three kinds, and it is also said that the three kinds of depression is likely to appear while interacting with each other (refer to Japanese Cabinet Office "White Paper on National Life (2008)", Chapter 1, Section 3, "2. Stressful Society and Modern pathology, "http://www5.cao.go.jp/seikatsu/whitepaper/h20/10_pdf/01_honpen/pdf/08sh_0103_03.pdf). It can be said that a pregnant woman is under an environment allowing all the above kinds (1) to (3) of cause to be likely to be filled. During a gestation period, a pregnant woman cannot take a medicine and has restrictions on exercise, so that stress is less likely to be resolved. This may cause a pregnant woman to have a mental disorder such as a depression.

There is also a report that a postpartum depression is likely to appear within two weeks after giving birth (refer to General Conference (2013), Special Lectures, "Grasping Metal Problem of Pregnant Woman and Child Care", Keiko Yoshida, Child Health in Okinawa, vol. 41 (2014) p. 3-8, http://www.osh.or.jp/in_oki/pdf/41gou/kouen.pdf). Thus, it is important to grasp a sign of a postpartum depression during a gestation period to prevent a postpartum depression.

In consideration of the above, the present inventors have researched prevention of postpartum depression by developing a tool of objectively grasping a level of stress accumulated on a pregnant woman before childbirth.

Here, cortisol, which is generally well known in relationship with stress, will be mentioned. The cortisol is a hormone that increases in secretion volume when a person is subjected to excessive stress. Thus, an inspection of a concentration of the cortisol enables an amount of stress at the time of the inspection to be grasped. The concentration of the cortisol can be measured by collecting saliva or blood, or by urine analysis. For example, a cumulative secretion volume of cortisol per day can be measured by collecting urine for 24 hours, so that an amount of stress per day also can be evaluated.

When the cortisol has a high concentration, Cushing's syndrome, stress, depression, anorexia nervosa, and the like are suspected. Meanwhile, when the cortisol has a low concentration, Addison's disease, congenital adrenal hyperplasia, ACTH psychosis, pituitary adrenocortical insufficiency, and the like are suspected.

As described above, while a concentration of cortisol is effective to evaluate stress, it is difficult to grasp temporal change in concentration of the cortisol due to unreality of continuous collection of saliva or blood, or continuous urine analysis. Thus, it is also difficult to grasp temporal change in stress on a test subject.

Then, the present inventors set a hypothesis that biogas discharged from a skin surface of a person exists as an evaluation index of stress instead of the cortisol when mind and body are subjected to stress. To verify the hypothesis with an experiment, the present inventors performed experiments to specify biogas that has a correlation with stress.

Specifically, the present inventors allow each of thirty test subjects to perform a task for causing them to feel stress, and during a predetermined period of time before and after performing the task, saliva was collected from each of the test subjects and biogas was collected from an armpit and a hand of each of the test subjects at a predetermined time interval. Then, the present inventors made temporal change in concentration of cortisol acquired from the saliva collected as described above into a graph, and identified a test subject showing prominent temporal change in concentration of cortisol concentration. It was recognized that the test subject identified here felt stress with the task above.

Next, the present inventors analyzed about 300 kinds of biogas collected from a hand of the test subject having felt stress in the above experiment to select a plurality of kinds of biogas being likely to have a correlation with stress. It was found that when stress was felt, furfural was discharged from skin, by measuring the amount of the biogas discharged during performing the task and after performing the task in the biogas selected here, a procedure in which furfural is determined to be less likely to be discharged from the skin of the test subject when the test subject feels stress will be described.

The present inventors built a psychology laboratory. The psychology laboratory is provided its inside with an isolated small room. The inside of the isolated small room can be seen from the outside thereof only through a glass window. The isolated small room is designed to apply psychological pressure to a test subject when a stress task is performed.

The present inventors guided thirty Japanese women in their twenties to forties serving as test subjects one by one into the psychology laboratory. Then, saliva of each of the test subjects was collected in the psychology laboratory. In ten minutes after saliva was collected from a test subject, the test subject grappled stress tasks such as a calculation problem, a speech, and the like for twenty minutes. For thirty minutes immediately after finish of the stress tasks, saliva was collected from the test subject once every ten minutes, i.e., four times in total. For the saliva collected here, a concentration of cortisol in each saliva was measured using a saliva cortisol quantitative kit (Salimetrics, LLC).

In parallel with the collection of saliva, biogas was collected from two places, a hand and an armpit, of the test subject for twenty minutes during the stress tasks and for twenty minutes from ten minutes to thirty minutes after the finish of the stress tasks. The biogas was collected from the hand by laying a gas-sampling bag on the hand of the test subject while fixing a wrist of the test subject with a rubber band, the inside of the gas sample bag being provided with an absorbent body for absorbing the biogas. The biogas was collected from the armpit by allowing the test subject to hold absorbent in the armpit. The absorbent held in the armpit was enclosed with cotton, and was fixed with a packing bag to prevent a position of the absorbent from being displaced in the armpit. The biogas was collected from the hand and the armpit as described above because sweat glands are concentrated in the hand and the armpit. Besides the hand and the armpit described above, the biogas may be collected from any portion in a skin surface.

In a day different from the day when the stress tasks were performed, the relaxation task was performed in place of the stress tasks. The relaxation task was performed according to procedures similar to those in the day when the stress tasks were performed to collect saliva and biogas from the test subjects. The relaxation task here was a work that caused the test subjects each to watch a DVD of natural scenery.

FIG. 1 is a graph showing temporal change in concentration of cortisol in saliva of the test subject before and after the stress task, and before and after the relaxation task. The vertical axis represents concentration (μg/dL) of cortisol, and the horizontal axis represents time (minute) from start of the stress task or the relaxation task. The concentration of cortisol increases upward in the vertical axis in FIG. 1, and as the concentration of cortisol increases, a test subject felt stress more as described above. The shaded portion in the graph of FIG. 1 (0 min. to 20 min. in the horizontal axis) is a period of time in which the stress task or the relaxation task was performed. As a publicly known fact, it is known that a concentration of cortisol in saliva increases in about 15 minutes after a test subject feels stress.

While in the graph of FIG. 1, the concentration of cortisol suddenly rises in 20 minutes after the start of the stress task (i.e., immediately after the finish of the stress task), there is little change found in the concentration of cortisol before and after the relaxation task. As a result, it is conceivable that the test subject showing the temporal change in the concentration of cortisol in FIG. 1 felt stress due to the stress task.

Meanwhile, there was a test subject who did not show temporal change in concentration of cortisol as described in FIG. 1. It is conceivable that this kind of test subject felt no stress due to the task to cause no cortisol in saliva to be secreted. Even when biogas of the test subject having felt no stress as described above is evaluated, a cause and effect relationship between stress and the biogas cannot be grasped. Thus, a test subject having felt no stress was eliminated from an evaluation object of the biogas. As described above, the top twenty test subjects (test subjects No. 1 to 20) having concentration of cortisol suddenly rising before and after the stress task among the thirty test subjects were identified.

Figure 2:
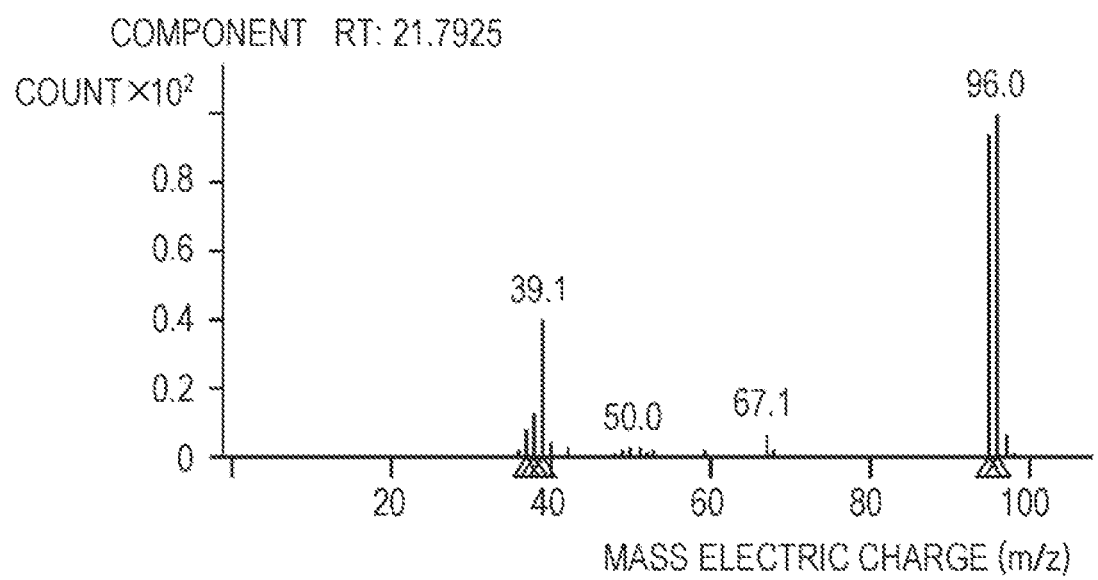
FIG. 2 shows mass spectrum data on furfural collected from a hand of a certain test subject.
Figure 3:
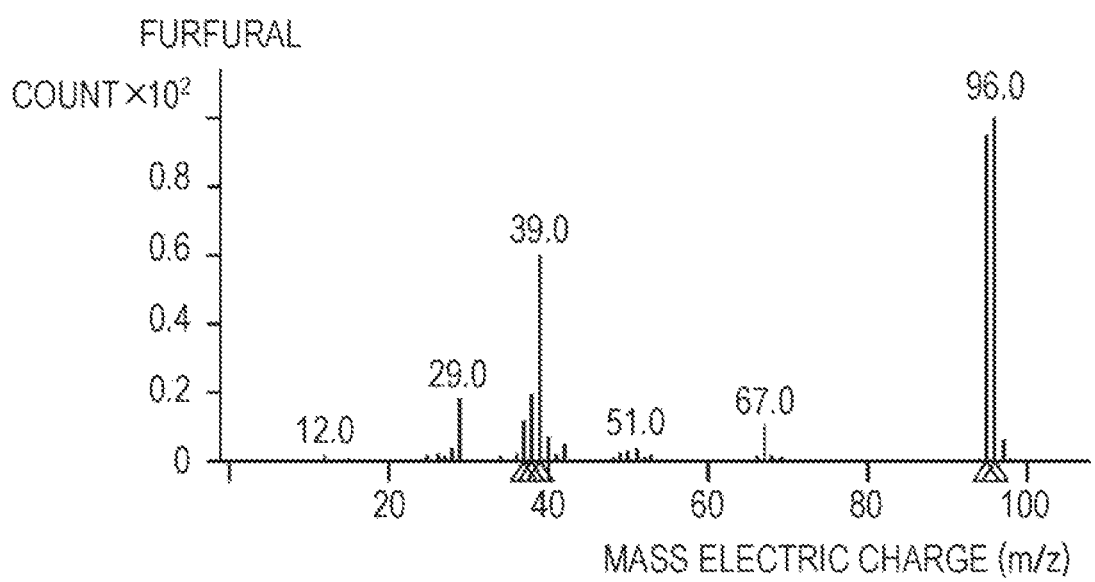
FIG. 3 shows mass spectrum data on furfural in the national institute of standards and technology (NIST) database.

Each of the absorbents collected (during and after the stress task, and during and after the relaxation task) from a hand of each of the test subjects identified above was heated to desorb biogas of each of the test subjects, which had been absorbed in the corresponding one of the absorbents. Then, the desorbed biogas was analyzed with a gas chromatography-mass spectrometry (GC/MS (made of Agilent Technologies, Inc.)) to acquire mass spectrum data on the biogas. The mass spectrum data was compared with the national institute of standards and technology (NIST) database using analysis software of Agilent Technologies, Inc. to identify furfural. FIG. 2 shows mass spectrum data on furfural in biogas, and FIG. 3 shows mass spectrum data on furfural in the NIST database. In comparison between the mass spectra in FIGS. 2 and 3, a similar spectrum peak is observed at an almost identical mass electric charge (miz). As described above, it was identified that furfural was contained in the biogas.

Next, the present inventors calculated a peak area of a mass spectrum of each biogas discharged from a hand of the corresponding one of the twenty test subjects (test subjects No. 1 to 20) during and after the stress tasks, as well as during and after the relaxation task, for each of the twenty test subjects above, and compared the peak area of each biogas during and after the stress tasks with that during and after the relaxation task to select a plurality of substances as candidates associated with stress from among components of the biogas, more than 300 kinds. Among the candidate substances, it was clearly found that furfural had a correlation with stress. The furfural has a chemical formula as follows.

CHEMICAL FORMULA 1

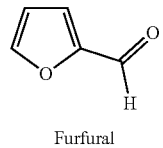

Furfural

Figure 5:
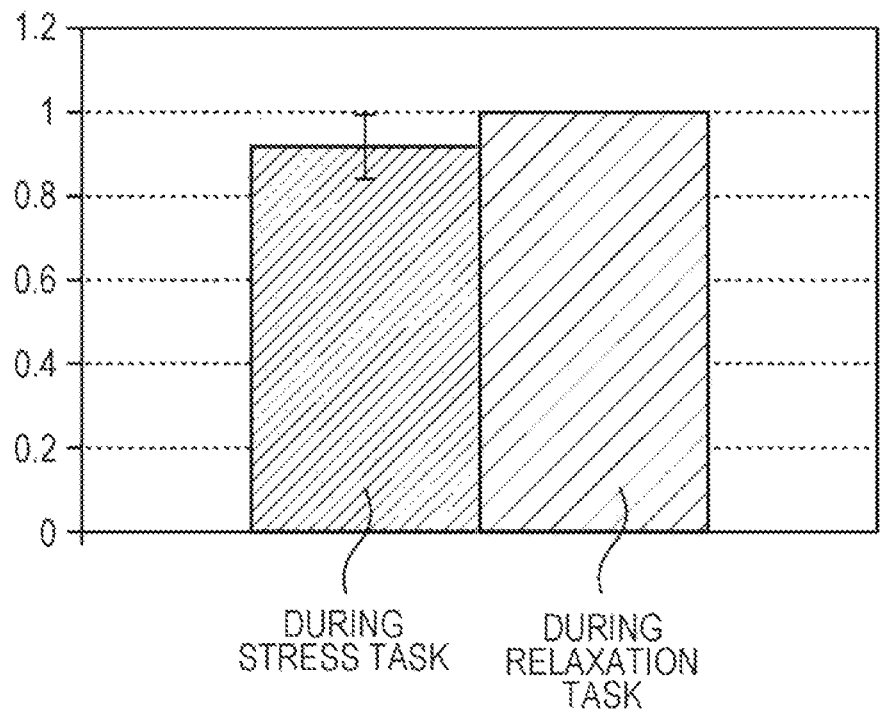
FIG. 5 is a bar graph showing an average value of relative values of respective peak areas and a deviation range, in the list of FIG. 4.

Next, a peak area of the furfural was calculated from the mass spectrum acquired with the GC/MS in each condition described above. A table shown in FIG. 4 is a list showing a ratio of peak areas of furfural in mass spectrum data acquired when biogas collected from the hand of each of test subjects during the stress task is analyzed with the GC/MS by assigning 1 to a peak area of furfural in mass spectrum data acquired when biogas collected from the hand of each of the test subjects during the relaxation task is analyzed with the GC/MS. FIG. 5 is a bar graph showing an average value of relative values of respective peak areas and a deviation range, in the list of FIG. 4. As shown in FIGS. 4 and 5, when a peak area of the furfural corrected during the relaxation task is assigned as 1, a ratio of a peak area of the furfural corrected during the stress tasks is less than 1.

From the results above, it was revealed that furfural was less likely to be discharged from the hand of the test subject during the stress tasks as compared with that during the relaxation task. As a result, it can be said that the amount of discharge of furfural has a correlation with stress on the test subject. Thus, furfural can serve as an index to objective evaluation of the amount of stress on a test subject. According to recognition of the present inventors, there is no example such as document about research associating the selected furfural with stress prior to the filing of the present application.

Next, a device for detecting furfural has been developed to succeed in objectively capturing stress that has been felt subjectively. That is, a method for measuring furfural discharged from a skin surface of a person with a device such as a sensor enables continuous measurement. In this case, it can be grasped when a stress reaction occurs in a day, what the person does when the stress reaction occurs, and the like. This enables temporal change in stress to be objectively grasped, so that it is expected that the stress can be controlled.

In addition, the present inventors have to lead the fact that measuring biogas caused by stress enables stress to be objectively grasped to a final purpose of preventing postpartum depression. Each aspect of the invention according to the present disclosure relates to the above.

Based on the new findings acquired by the earnest research performed by the present inventors as described above, the present inventors have conceived each aspect according to the invention.

An aspect of the invention according to the present disclosure is a method for providing information in an information processing system, the method comprising:

acquiring, via a network, biogas information representing a concentration of furfural of a user acquired by a sensor that detects the furfural discharged from a skin surface of the user;

obtaining reference information representing a lower limit of a normal range of the concentration of furfural per unit period of time, using a memory storing the reference information representing the lower limit of the normal range; and outputting information related to stress on the user to an information terminal after it is determined that a frequency with which the concentration of the furfural of the user per unit period of time is less than the lower limit of the normal range tends to increase, based on the biogas information acquired in a pregnancy period of the user.

PTL 1 uses information in a maternal and child health handbook. The information in a maternal and child health handbook is less likely to be objective information for determination, because the information is subjectively written by a pregnant woman, a doctor, a hygienist of a local government, and the like. For example, even under stress, no stress being felt may be described. Likewise, even under no stress, large stress being felt may be described. In addition, under an environment with stress always, for example, it is also conceivable that feeling stress becomes insensitive.

In contrast, in the present aspect, the amount of stress is objectively determined using furfural that is biogas estimated to have a relationship with stress. This enables a sign of postpartum depression to be objectively grasped without being affected by subjective feeling of a pregnant woman.

As a result, when it is determined that a frequency of appearance of concentration of furfural of the user in the unit period of time less than the lower limit of the normal range tends to increase, information related to stress of the user is output to an information terminal. This enables a pregnant woman herself to objectively recognize a sign of postpartum depression in a pregnancy period, so that prevention of the postpartum depression can be expected.

The term "pregnancy period" means a period of time from the first day of the latest menstruation to childbirth (parturition). However, there is a report that postpartum depression is likely to appear in two weeks after childbirth, so that the end period of the "pregnancy period" may be defined as two weeks after childbirth in the present specification.

the lower limit of the normal range of the concentration of furfural per unit period of time may be set for the user as individual information of the user, based on the biogas information acquired in a predetermined period of time in an early stage of the pregnancy period of the user.

In this case, data on the user itself is used as a reference value. The amount of discharge of furfural being biogas is affected by age, food, weight, and the like to cause an individual difference, so that it is preferable to use data on the user itself for accurate determination.

In contrast, a reference value common to all users is used in PTL 1.

According to the present aspect, a sign of postpartum depression is determined using data on the user itself as a reference value. This enables determination suitable for an individual pregnant woman.

In the present aspect, the lower limit of the normal range of the concentration of furfural per unit period of time may be used commonly to a plurality of users including the user.

In this case, the reference value is used common to a plurality of users to save time for creating and managing a reference value for each of the users.

In the present aspect, when it is not determined that the frequency that the concentration of the furfural of the user per unit period of time is less than the lower limit of the normal range tends to increase, the information related to stress on the user does not have to output to the information terminal.

This case enables information related to stress to be prevented from being output to the information terminal when no sign of postpartum depression is found out.

In the present aspect, the information terminal may be a first information terminal of the user.

In this case, the information terminal is composed of the first information terminal of the user. Accordingly, when a sign of postpartum depression is found out in a pregnancy period, a pregnant woman itself can objectively recognize the sign, thereby enabling prevention of postpartum depression to be expected.

In the present aspect, the information terminal may be a second information terminal of a counseling business operator other than the first information terminal of the user.

In this case, the information terminal is composed of the second information terminal of the counseling business operator. Accordingly, when a sign of postpartum depression is found out in a pregnancy period, the counseling business operator is allowed to objectively recognize the sign, thereby enabling the counseling business operator to take measures such as taking care of a pregnant woman. As a result, prevention of postpartum depression can be expected.

Further, in the present aspect, the information terminal may be a first information terminal of the user. The method may further include:

acquiring first address information on the first information terminal and second address information on the consulting business operator from a memory storing the first address information and the second address information, when it is determined that the frequency that the concentration of furfural of the user per the unit period of time is more than the upper limit of the normal range tends to increase; and outputting the information related to stress of the user to both of the first information terminal and a second information terminal of the consulting business operator, based on the first address information and the second address information, wherein the second information terminal of the consulting business operator is distinct from the first information terminal.

In this case, when a sign of postpartum depression is found out in a pregnancy period, information related to stress is output to both of a pregnant woman and a counseling business operator. This enables the pregnant woman to recognize that there is the sign of postpartum depression and the counseling business operator to take care of the pregnant woman. As a result, prevention of postpartum depression can be further expected.

In the present aspect, the information to be output to the first information terminal may include display information for allowing the user to select whether to accept contact of the counseling business operator with the user.

Some users do not desire to be taken care of a counseling business operator. In the present aspect, a user can select whether to accept access of the counseling business operator, so that needs of the user can be flexibly handled.

In the present aspect, the information related to the stress on the user may be used to call the user's attention to a need for reducing stress build up in the user.

In this case, the information indicating that stress requires attention is notified to the user. This enables the user to early recognize accumulation of stress to prevent postpartum depression.

In the present aspect, the information related to the stress on the user may indicate that stress on the user is less than the lower limit of the normal range.

In this case, the information indicating that stress of the user is less than the lower limit of the predetermined normal range is notified to the user. This enables information objectively indicating that stress is accumulated in the user to be notified to the user, so that the user can effectively recognize that there is a sign of postpartum depression.

In the present aspect, the sensor for detecting furfural may be built in a device to be worn by the user.

In this case, the sensor for detecting furfural is built in the device worn on an arm of the user, so that an object worn on the arm of the user in daily life may have a function of the sensor, for example. As a result, user's inconvenience of wearing a sensor can be reduced.

In the present aspect, the information processing system may be configured to acquire the biogas information along with a user ID of the user, and to output the information related to stress on the user to the information terminal associated with the user ID of the user.

In this case, the biogas information is acquired along with the user ID, so that the biogas information can be managed for each user. This enables determination of a sign of postpartum depression of a user using biogas information on another user to be prevented. In addition, the information related to stress is transmitted to the information terminal related to the user ID, so that the information related to stress can be prevented from being transmitted to an information terminal that is not associated with the user ID, thereby enabling privacy of the user to be protected.

An information processing system according to another aspect of the present disclosure includes a server device and an information terminal, wherein the server device may acquire biogas information showing a concentration of furfural of a user acquired by a sensor that detects the furfural discharged from a skin surface of the user; read out information showing a lower limit of a normal range of the concentration of furfural per unit period of time from a memory storing the information showing the lower limit of the normal range; and output information related to stress of the user to the information terminal when it is determined that a frequency of appearance of concentration of furfural of the user in the unit period of time less than the lower limit of the normal range tends to increase, based on the biogas information acquired in a pregnancy period of the user, and the information terminal may display the information related to stress of the user in a display of the information terminal.

An information terminal according to yet another aspect of the present disclosure is used in the information processing system described above.

An information processing method according to yet another aspect of the present disclosure uses a computer, the information processing method including acquiring biogas information showing a concentration of furfural of a user acquired by a sensor that detects the furfural discharged from a skin surface of the user; reading out information showing a lower limit of a normal range of the concentration of furfural per unit period of time from a memory storing the information showing the lower limit of the normal range; and outputting information related to stress of the user to display the information in a display when it is determined that a frequency of appearance of concentration of furfural of the user in the unit period of time less than the lower limit of the normal range tends to increase, based on the biogas information acquired in a pregnancy period of the user.

The present aspect assumes that a local computer performs processing, for example.

First Embodiment

Estimated Data

Figure 6A:
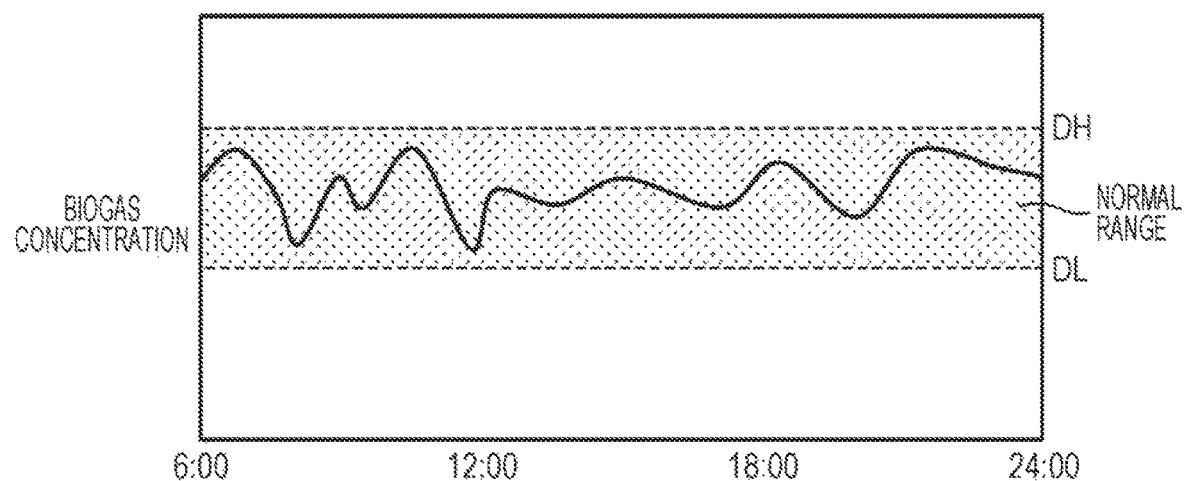
FIG. 6A is a graph showing estimated data on biological data used in a first embodiment of the present disclosure.
Figure 6B:
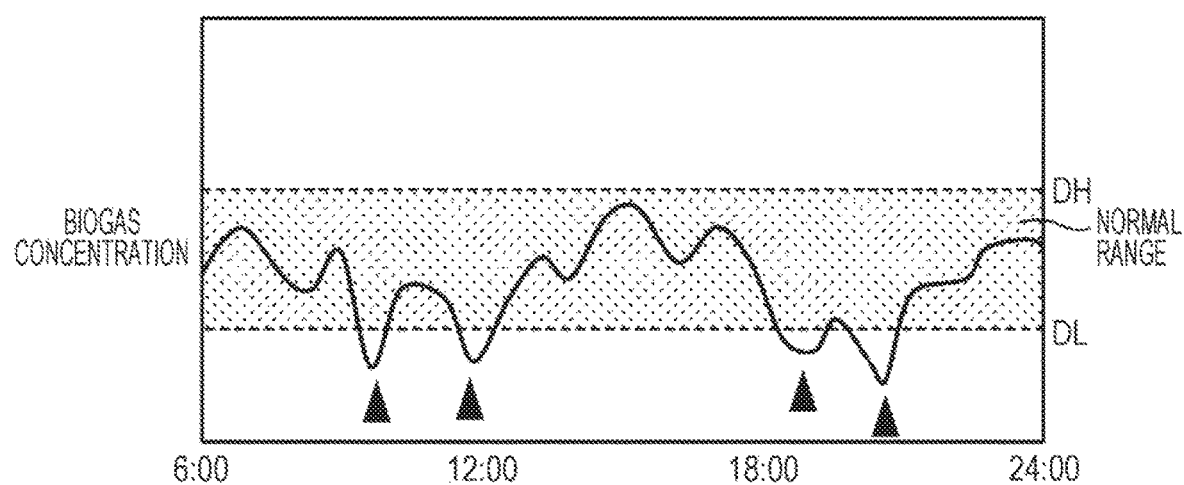
FIG. 6B is a graph showing estimated data on biological data used in the first embodiment of the present disclosure.

FIGS. 6A and 6B are each a graph showing estimated data on biological data used in the first embodiment of the present disclosure. In each of FIGS. 6A and 6B, the vertical axis represents biogas concentration (an example of biogas information), and the horizontal axis represents time. The estimated data does not show measurement values of biological data that are actually measured, and is only data acquired by estimating the biological data. The biological data is measured by a sensor worn by a user as described below. The biological data shows a measurement value of concentration of biogas to be measured (biogas concentration) among biogas discharged from a skin surface of a user. In the present disclosure, the biogas to be measured is furfural. The biogas concentration has a unit of μg/dL, for example.

FIG. 6A shows a temporal transition of biological data on a user without stress, and FIG. 6B shows a temporal transition of biological data on the user with stress. As shown in FIG. 6A, the biological data without stress has biogas concentration within a normal range. In contrast, as shown in FIG. 6B, the biological data with stress has biogas concentration that is frequently less than lower limit DL of the normal range. FIG. 6B shows an example in which the biogas concentration is less than lower limit DL four times in a time period from six o'clock to twenty-four o'clock.

Then, in the present disclosure, when it is detected that a frequency of appearance of biogas concentration less than lower limit DL tends to increase, it is determined that the user has a sign of postpartum depression. This allows the user to recognize that there is a sign of postpartum depression, or a counseling business operator to take care of the user, so that the user is prevented from having postpartum depression.

Sensor

Figure 7:
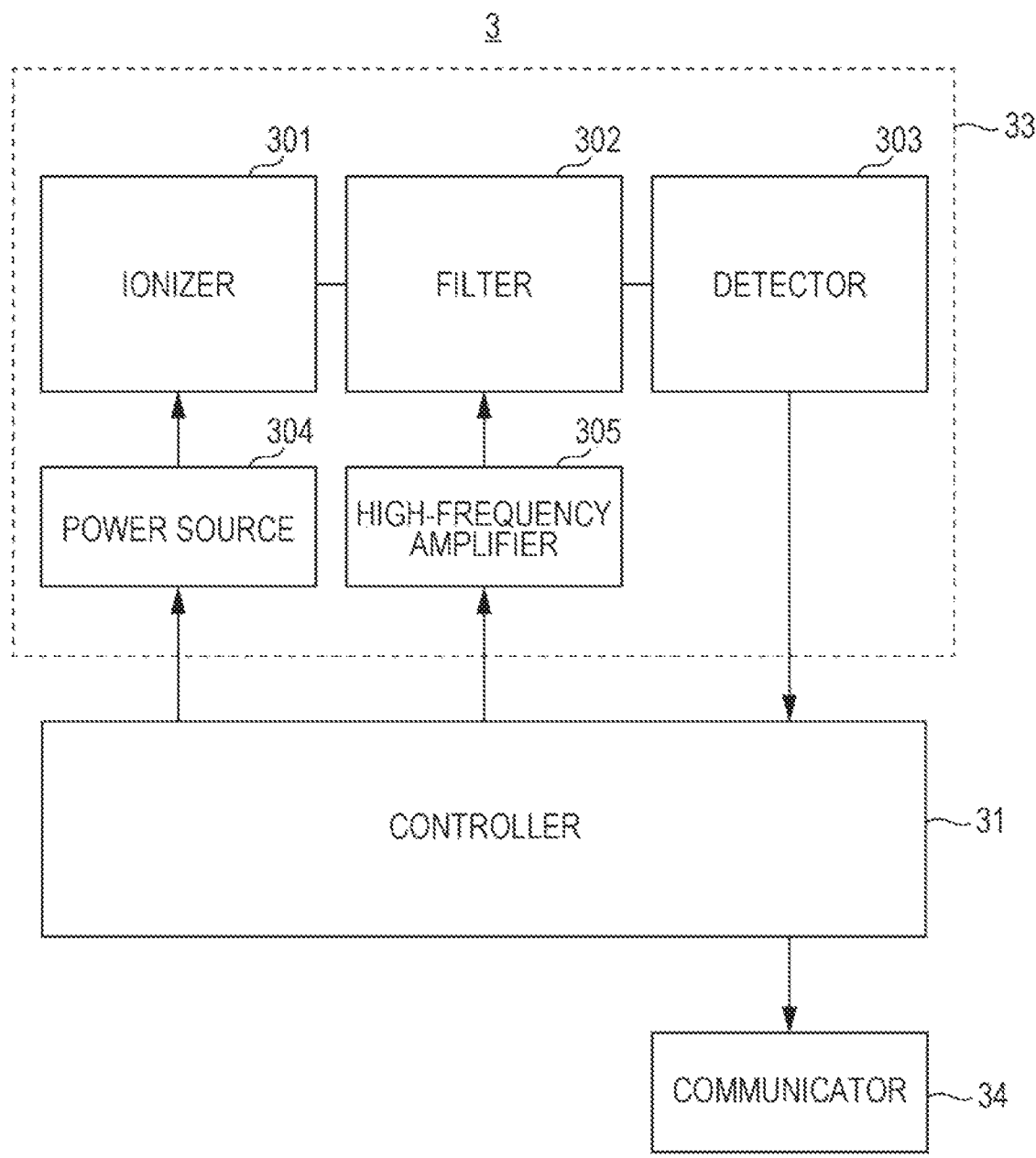
FIG. 7 is a block diagram illustrating an example of a configuration of a sensor that measures biological data in the first embodiment of the present disclosure.

FIG. 7 is a block diagram illustrating an example of a configuration of sensor 3 that measures biological data in the first embodiment of the present disclosure.

In the present disclosure, a sensor using a technique of field asymmetric ion mobility spectrometry (FAIMS) is used as the sensor 3, for example. The field asymmetric ion mobility spectrometry is used to selectively separate at least one kind of substance from a mixture containing two or more kinds of substance.

Sensor 3 includes detector 33, controller 31, and communicator 34. Detector 33 comprises ionizer 301, filter 302, detector 303, power source 304, and high-frequency amplifier 305. In FIG. 7, arrows each indicate a flow of an electric signal, and lines connecting ionizer 301, filter 302, and detector 303 indicate a flow of biogas.

Power source 304 and high-frequency amplifier 305 are used to drive ionizer 301 and filter 302, respectively. Filter 302 separates only desired biogas (furfural in the present disclosure) from among biogas ionized using ionizer 301, and detector 303 detects the amount of ions which has passed through filter 302 so that information indicating biogas concentration is acquired. The information acquired is output via communicator 34. Driving of sensor 3 is controlled by controller 31.

Figure 8:
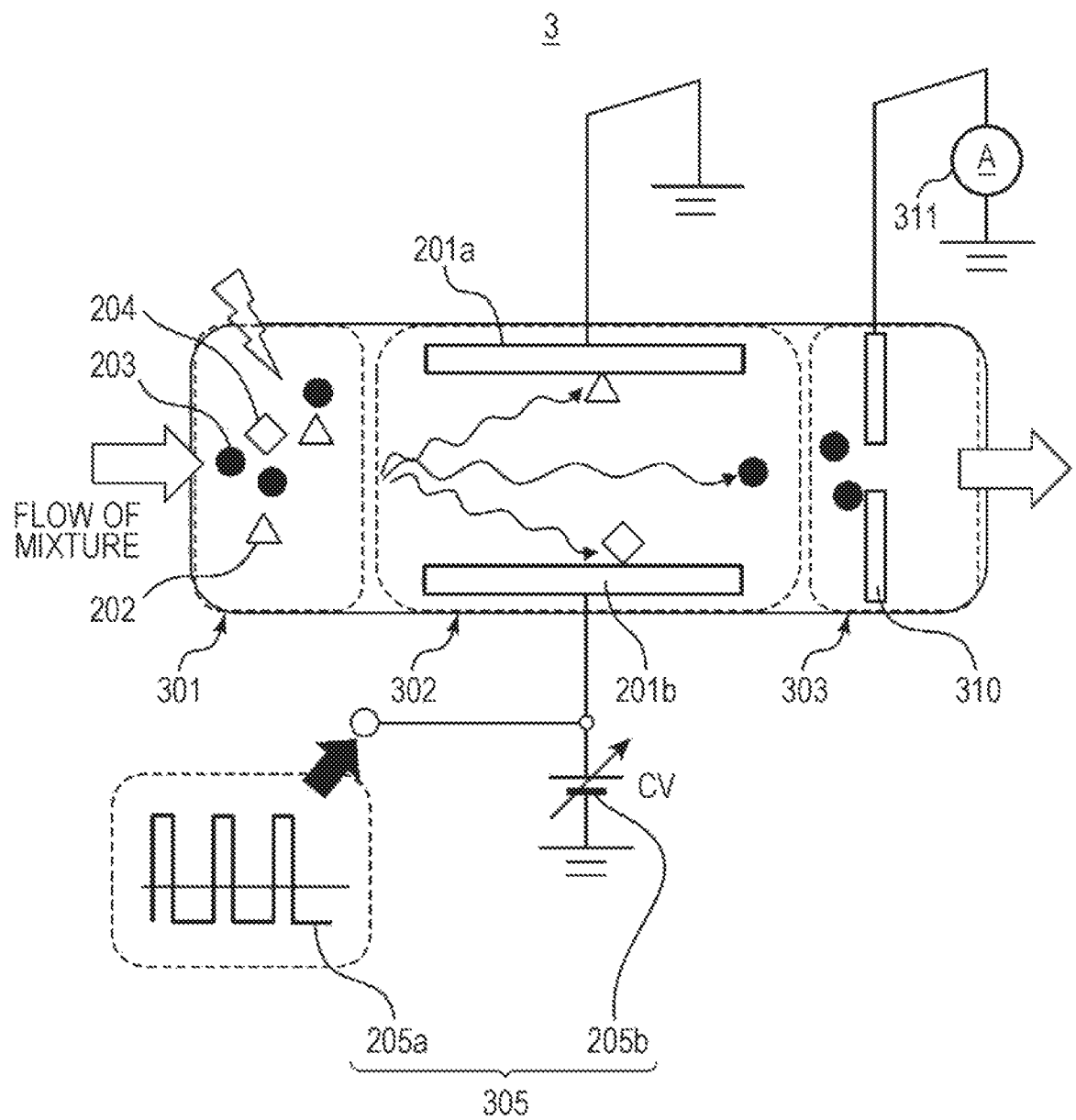
FIG. 8 illustrates operation of the sensor illustrated in FIG. 7 in more detail.

FIG. 8 illustrates operation of sensor 3 illustrated in FIG. 7 in more detail. A mixture supplied to ionizer 301 is biogas discharged from a skin surface of a user. Ionizer 301 may include an inlet for taking in biogas discharged from a skin surface of a user. The inlet may be provided with absorbent for absorbing biogas. The inlet may be further provided with a heater for separating biogas absorbed in the absorbent from the absorbent. FIG. 8 shows an example in which the mixture contains three kinds of gas 202 to 204, for convenience of explanation. Gas 202 to 204 is ionized using ionizer 301.

Ionizer 301 comprises a corona-discharging source, a radiation source, and the like to ionize gas 202 to 204. Gas 202 to 204 ionized is supplied to filter 302 disposed adjacent to ionizer 301. The corona-discharging source and the radiation source, constituting ionizer 301, are driven by voltage supplied from power source 304.

Filter 302 comprises first electrode 201a in a planar shape and second electrode 201b in a planar shape, being disposed parallel to each other. First electrode 201a is grounded. Meanwhile, second electrode 201b is connected to high-frequency amplifier 305.

High-frequency amplifier 305 includes AC voltage source 205a that generates asymmetric AC voltage, and variable voltage source 205b that generates compensation voltage CV being DC voltage. AC voltage source 205a generates asymmetric AC voltage and applies it to second electrode 201b. Variable voltage source 205b is connected at one end to second electrode 201b, and at the other end to the ground. Then, the asymmetric AC voltage generated by AC voltage source 205a is superposed on compensation voltage CV, and is supplied to second electrode 201b.

Three kinds of gas 202 to 204 ionized are supplied to a space between first electrode 201a and second electrode 201b. Three kinds of gas 202 to 204 are affected by an electric field generated between first electrode 201a and second electrode 201b.

Figure 9:
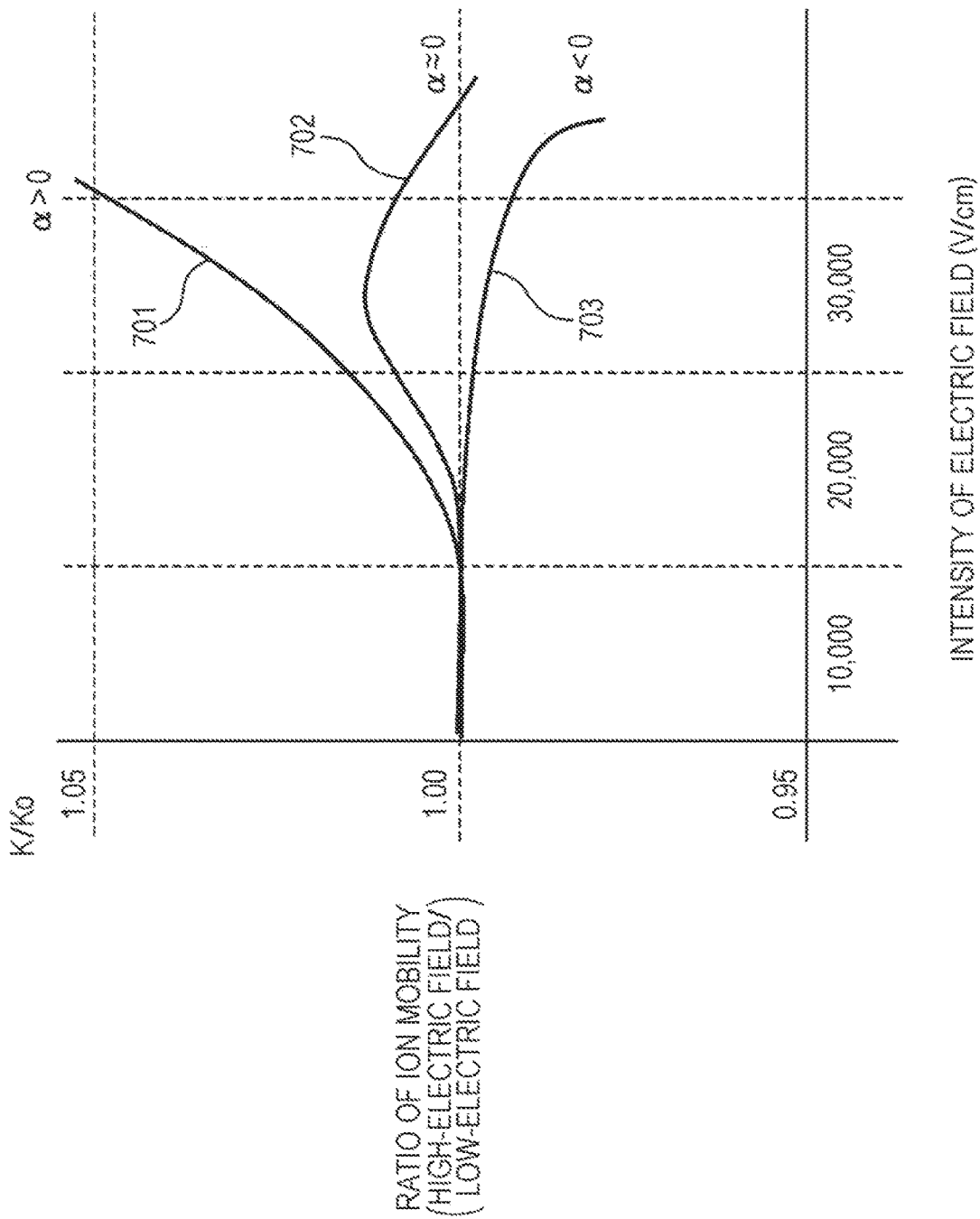
FIG. 9 is a graph showing a relationship between intensity of an electric field and a ratio of ion mobility.

FIG. 9 is a graph showing a relationship between intensity of an electric field and a ratio of ion mobility, its vertical axis representing the ratio of ion mobility, and its horizontal axis representing intensity (V/cm) of the electric field. $\alpha$ is a coefficient determined depending on a kind of ion. The ratio of ion mobility is a ratio of mobility in a high-electric field to mobility in a boundary of a low-electric field.

As indicated by curve 701, ionized gas with a coefficient $\alpha$ more than zero moves more actively as intensity of electric field increases. An ion with a mass-to-charge ratio less than 300 shows this kind of movement.

As indicated by curve 702, ionized gas with a coefficient $\alpha$ of almost zero moves more actively as intensity of electric field increases, however, the mobility decreases in mobility as the intensity of the electric field further increases.

As indicated by curve 703, ionized gas with a negative coefficient $\alpha$ decreases in mobility as intensity of electric field increases. An ion with a mass-to-charge ratio of 300 or more shows this kind of movement.

Due to difference in characteristics of mobility as described above, each of three kinds of gas 202 to 204 proceeds inside filter 302 in a different direction as illustrated in FIG. 8. FIG. 8 illustrates an example in which while only gas 203 is discharged through filter 302, gas 202 is trapped on a surface of first electrode 201a, and gas 204 is trapped on a surface of second electrode 201b. As a result, only gas 203 is selectively separated from three kinds of gas 202 to 204, and discharged through filter 302. That is, sensor 3 can discharge desired gas through filter 302 by appropriately setting intensity of the electric field. The intensity of the electric field is determined in accordance with a voltage value of compensation voltage CV and a waveform of asymmetric AC voltage generated by AC voltage source 205a. Thus, sensor 3 can discharge biogas to be measured through filter 302 by setting the voltage value of compensation voltage CV and the waveform of asymmetric AC voltage, respectively, to a voltage value and a waveform, predetermined in accordance with a kind of the biogas to be measured (furfural in the present disclosure).

Detector 303 is disposed adjacent to filter 302. That is, filter 302 is disposed between ionizer 301 and detector 303. Detector 303 comprises electrode 310 and ammeter 311 to detect gas 203 having passed through filter 302.

Gas 203 which has reached detector 303 transfers electric charge to electrode 310. A value of an electric current which flows in proportion to the amount of the transferred electric charge is measured with Ammeter 311. From the value of the electric current measured by ammeter 311, a concentration of gas 203 is measured.

Network Configuration

Figure 10:
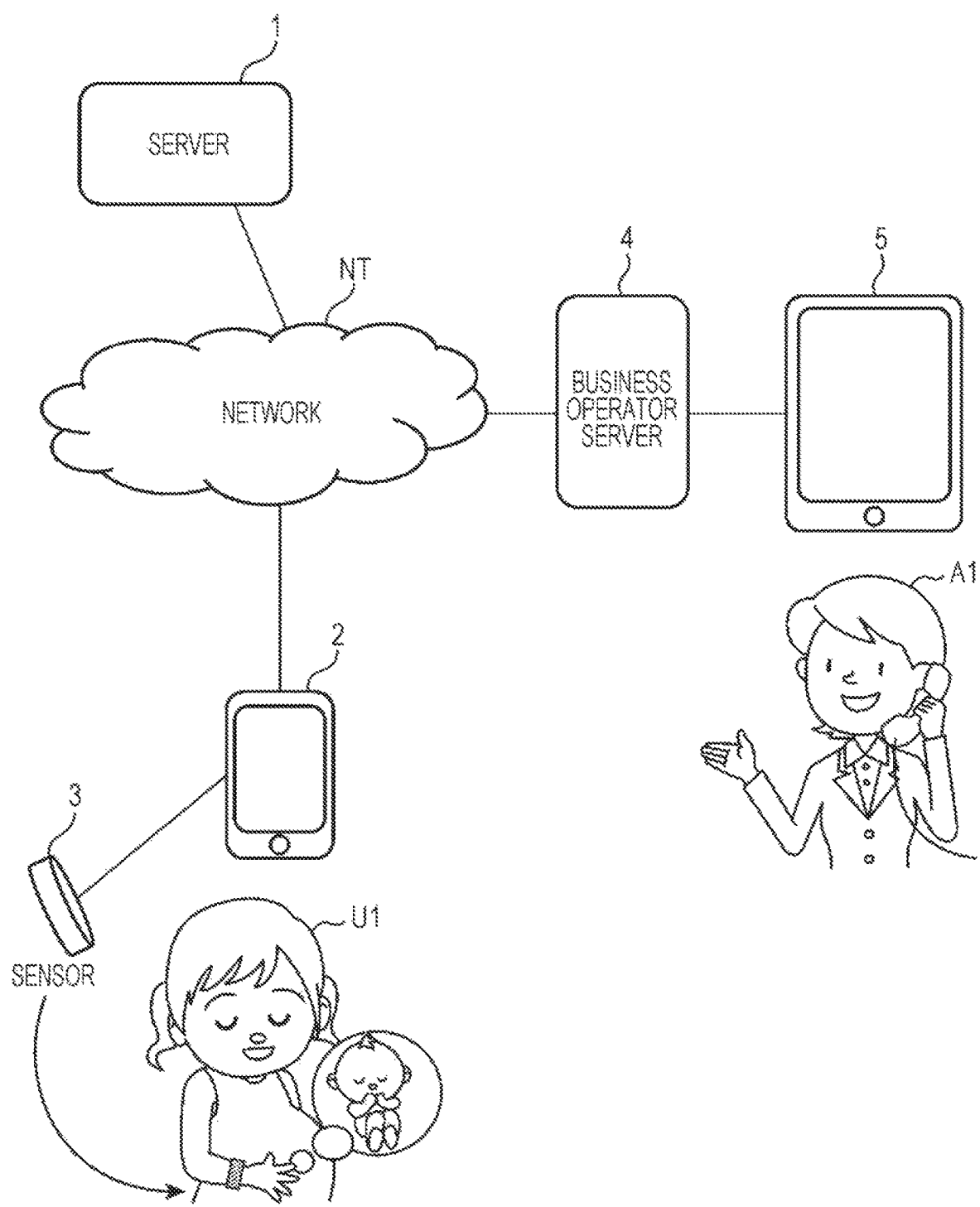
FIG. 10 illustrates an example of a network configuration of an information processing system according to the first embodiment of the present disclosure.

FIG. 10 illustrates an example of a network configuration of an information processing system according to the first embodiment of the present disclosure. The information processing system provides a care service for taking care of stress on user U1. The care service is provided, for example, by an insurance company or the like with which user U1 is contracted. Actual operation of the care service may be performed, for example, by a manufacturer that manufactures sensor 3 commissioned by the insurance company. The care service may be provided by a service provider different from an insurance company providing the care service.

The insurance company provides insurance service such as life insurance and medical insurance to user U1, for example. Then, the insurance company lends sensor 3 to user U1, for example, and acquires biological data on user U1 to manage a state of stress on user U1, thereby preventing postpartum depression of user U1. This allows the insurance company to save expenditure for insurance. The care service urges user U1 to wear sensor 3, so that user U1 may feel a burden. Then, the insurance company may provide an insurance plan for reducing an insurance fee borne by user U1 in exchange for the care service.

The information processing system comprises server 1 (an example of the server device), user terminal 2 (an example of the first information terminal), sensor 3, business operator server 4, and business operator terminal 5 (an example of the second information terminal).

Server 1, user terminal 2, and business operator server 4 are communicatively connected to each other via network NT. Network NT is composed of the Internet communication network, a cellular phone communication network, and a network including a public telephone network. Sensor 3 and user terminal 2 are communicatively connected to each other, for example, via near field communication such as a wireless LAN of IEEE802.11b, or Bluetooth (registered trademark: IEEE802.15.1). In addition, business operator server 4 and business operator terminal 5 are communicatively connected to each other, for example, with a wired LAN (e.g., IEEE802.3), a wireless LAN (e.g., IEEE802.11b), or the like.

Server 1 is composed of a cloud server including one or more computers, for example. Server 1 includes a processor such as a CPU, an FPGA or the like, and a memory. Server 1 acquires biological data on user U1 measured with sensor 3 via user terminal 2 and network NT to determine whether biogas concentration is within the normal range.

User terminal 2 is composed of a portable information processor such as a smartphone, a tablet terminal, or the like, for example. The user terminal 2 may be composed of a desktop computer. User terminal 2 is possessed by user U1 In the present disclosure, user U1 is a pregnant woman who receives a care service, for example.

Business operator server 4 is composed of a cloud server including one or more computers, for example. Business operator server 4 includes a processor such as a CPU, an FPGA, or the like, and a memory. Business operator server 4 manages business operator terminal 5 by connecting business operator terminal 5 to network NT.

Business operator server 4 is managed by a counseling business operator to which staff A1 belongs, staff A1 taking care of user U1 using business operator terminal 5, for example. The counseling business operator may be a company commissioned by an insurance company, or an insurance company, for example. Staff A1 receives questions about an insurance service or a care service from user U1 by telephone or the like. Particularly, in the present disclosure, when a sign of postpartum depression appears in user U1, staff A1 communicates with user U1 under permission of user U1 to take care of user U1.

Sensor 3 is worn, for example, on an arm of user U1 to detect a concentration of biogas discharged from a hand of user U1. Sensor 3 includes a mounting belt, for example, and a user winds the mounting belt around its wrist (an example of an arm) to wear sensor 3 near the hand. This enables sensor 3 to detect biogas discharged from the hand. However, this is an example. For example, sensor 3 may be built in a wristwatch-type wearable terminal. Accordingly, the wristwatch-type wearable terminal is an example of a device to be worn by a user.

Business operator terminal 5 is composed of a desk-top type computer possessed by the counseling business operator, for example, and is used by staff A1. Business operator terminal 5 may be composed of a portable information processor such as a smartphone, a tablet terminal, or the like, for example.

Figure 11:
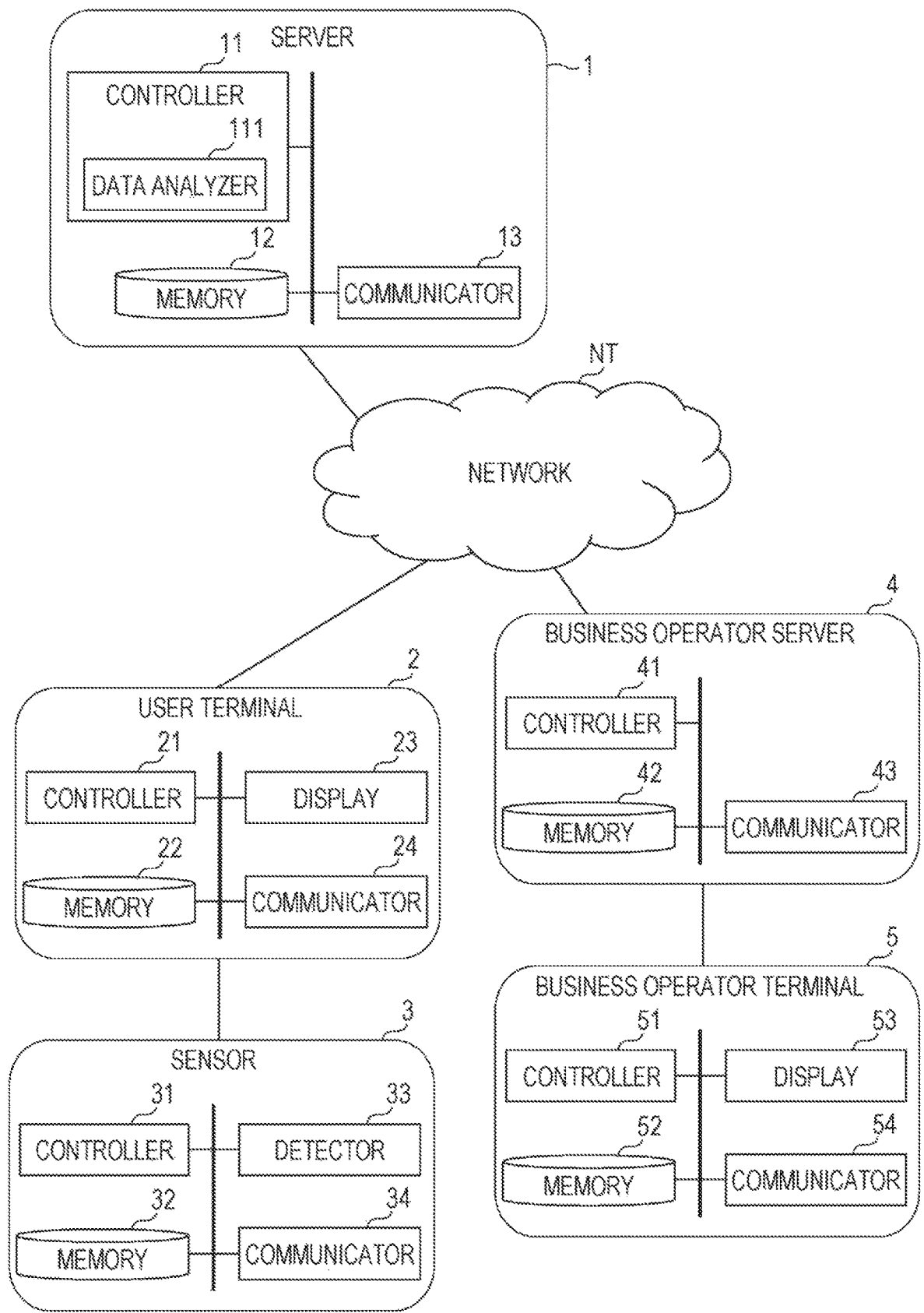
FIG. 11 is a block diagram illustrating an example of a detailed configuration of the information processing system illustrated in FIG. 10.

FIG. 11 is a block diagram illustrating an example of a detailed configuration of the information processing system illustrated in FIG. 10. Server 1 comprises controller 11, memory 12, and communicator 13. Controller 11 is composed of a processor, and comprises data analyzer 111. Data analyzer 111 serves when the processor executes a program for causing a computer to perform the information providing method of the present disclosure, the method being stored in memory 12, for example. The program for causing a computer to perform the information providing method of the present disclosure may be provided by download through a network, or may be provided by being stored in a computer-readable nontemporary recording medium.

When communicator 13 receives biological data acquired by sensor 3, data analyzer 111 acquires the biological data from communicator 13. Then, data analyzer 111 reads out information indicating lower limit DL of the normal range of biogas concentration from memory 12, and determines whether biogas concentration indicated by the biological data is less than lower limit DL. Subsequently, Data analyzer 111 registers the biological data in biological data table T4 (FIG. 12) stored in memory 12 while associating it with the determination result. In addition, when biological data for a predetermined period of time (e.g., one day, half a day, two days) is accumulated, data analyzer 111 counts the number of times when biogas concentration decreases to less than lower limit DL in the biological data for the predetermined period of time. Then data analyzer 111 compares the number of counts of times when biogas concentration decreases to less than lower limit DL for one or more consecutive prior predetermined periods of time, with the number of counts for the predetermined period of time at this time, to determine whether a frequency of appearance of biogas concentration less than lower limit DL tends to increase. When determining that the frequency tends to increase, data analyzer 111 transmits information related to stress to user terminal 2 and business operator terminal 5 via communicator 13.

Figure 12:
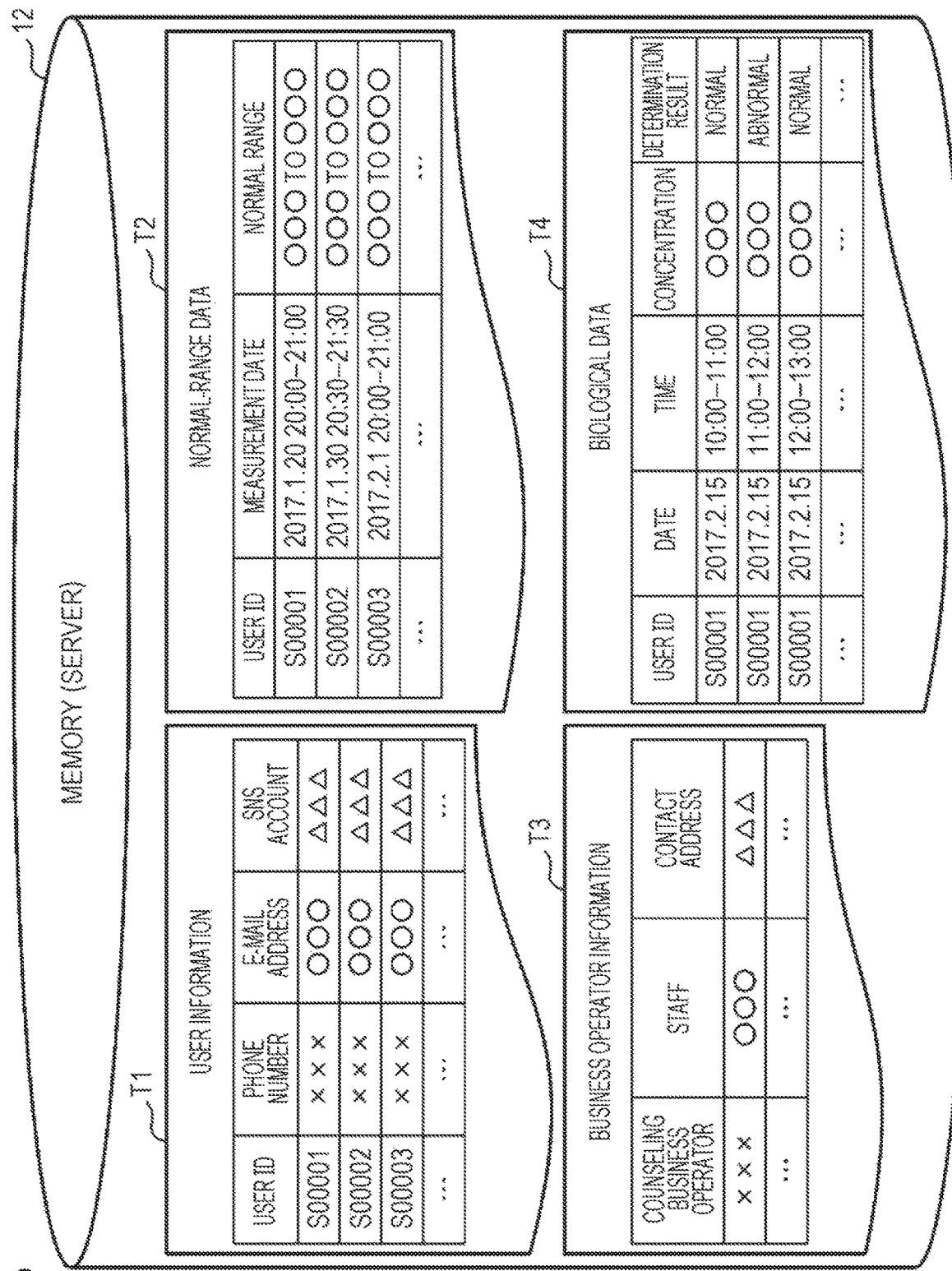
FIG. 12 illustrates an example of data organization of a table stored in a memory.

Memory 12 stores information indicating the normal range of biogas concentration. As illustrated in FIG. 12, memory 12 stores user information table T1, normal-range data table T2, business operator information table T3, and biological data table T4 in the present disclosure. FIG. 12 illustrates an example of data organization of a table stored in memory 12.

User information table T1 stores personal information on one or more users who each receive a care service. In user information table T1, one record is assigned to one user, and "user ID", "telephone number", "e-mail address", and "SNS account" are stored while being associated with each other. The "telephone number", the "e-mail address", and the "SNS account" are each an example of address information.

A "user ID" field stores an identifier for uniquely identifying a user receiving care service. A "telephone number" field stores telephone numbers of a user's home and user terminal 2. An "e-mail address" field stores an e-mail address of user terminal 2 of each user. An "SNS account" field stores account information to log on a social networking service (SNS) site opened by each user.

Normal-range data table T2 stores a normal range of stress in biogas concentration of one or more users receiving care service. In normal range data table T2, one record is assigned to one user, and "user ID", "measurement date and time", and "normal range" are stored while being associated with each other.

The "user ID" field stores a user ID identical to the user ID in user information table T1. A "measurement date" field stores a time period in a measurement date of biological data used for calculating a normal range. A "normal range" field stores the normal range calculated by using biological data stored in the "measurement date" field. The "normal range" field also stores lower limit DL and upper limit DH of the normal range.

With regard to a user with a user ID "S00001", the normal range thereof is calculated using biological data measured in a time period from twenty o'clock to twenty-one o'clock on Jan. 20, 2017

As described above, a normal range for each of users is calculated in the present disclosure, so that stress on each of the users can be determined using a normal range suitable for the corresponding one of the users to enable increase in determination accuracy. While the normal range for each of the users is calculated in the present disclosure, this is an example, and thus an average value of normal ranges calculated in a part of all the users may be used as a normal range for all the users. Alternatively; an average value of normal ranges of all the users may be used as a normal range for all the users. In these cases, a normal range is not required to be stored and calculated for each of the users, so that the amount of memory consumption can be saved and processing steps can be reduced.

Business operator information table T3 stores information on one or more counseling business operators. In business operator information table T3, one record is assigned to one counseling business operator. Business operator information table T3 stores "counseling business operator", "staff", and "contact address" while being associated with each other. A "counseling business operator" field stores a name of a counseling business operator. A "staff" field stores a name of a staff belonging to a counseling business operator. A "contact address" field stores a contact address of a staff. As the contact address of a staff, an e-mail address of business operator terminal 5 and a telephone number of the staff may be used. The "contact address" is an example of the address information.

Biological data table T4 stores biological data acquired by sensor 3. In biological data table T4, one record is assigned to one biological data, and "user ID", "date", "time", "concentration", and "determination result" are stored while being associated with each other.

The "user ID" field stores a user ID identical to the user ID stored in user information table T1. A "date" field stores a measurement date of biological data. A "time" field stores a time period in which the biological data is measured. A "concentration" field stores biogas concentration indicated by the biological data. A "determination result" field stores a result of determination whether the biogas concentration is within the normal range. The "time" field may store a time period in which server 1 acquires the biological data.

For example, in the record on the first line in the biological data table 4, biological data on biogas concentration "OO" of a user with a user ID "S00001", measured in a time period from ten o'clock to eleven o'clock on Feb. 15, 2017 is stored. In the first record, since the biogas concentration is within the normal range, "normal" is stored in the "determination result" field, because. Meanwhile, in the second record, since the biogas concentration out of the normal range, "abnormal" is stored in the "determination result" field.

While biological data table T4 shows only the biological data on the user with the user ID "S00001", this is only an example, and biological data table T4 stores biological data on all users receiving the care service.

FIG. 11 is referred again. Communicator 13 is composed of a communication circuit connecting server 1 to network NT, for example, and not only receives biological data measured with sensor 3, but also transmits information related to stress to user terminal 2 and business operator terminal 5.

User terminal 2 comprises controller 21, memory 22, display 23 (an example of the display), and communicator 24. Controller 21 is composed of a processor such as a CPU, and controls the whole of user terminal 2. The memory 22 stores various data. In the present disclosure, memory 22 particularly stores an application to be executed in user terminal 2 to cause user U1 to receive the care service. Memory 22 also stores a user ID transmitted in association with biological data.

Display 23 is composed of a display comprising a touch panel, for example, and displays various kinds of information. In the present disclosure, display 23 particularly displays information related to stress. Communicator 24 connects user terminal 2 to network NT, and is composed of a communication circuit for allowing user terminal 2 to communicate with sensor 3. In the present disclosure, communicator 24 particularly receives biological data transmitted from sensor 3, and transmits the received biological data to server 1 while associating it with a user ID stored in memory 22. In the present disclosure, communicator 24 particularly receives information related to stress transmitted from server 1. Display 23 does not have to be composed of a touch panel. In this case, user terminal 2 may include an operation section that receives operation from a user.

Sensor 3 comprises controller 31, memory 32, detector 33, and communicator 34. Controller 31 is composed of a processor such as a CPU, a DSP, or the like and controls the whole of sensor 3. Memory 32 temporarily stores biological data measured by detector 33, for example. Memory 32 also stores data (e.g., frequency, positive amplitude, and negative amplitude) required for AC voltage source 205$a$ to generate asymmetric AC voltage. Memory 32 also stores a voltage value of compensation voltage CV.

Communicator 34 is composed of a communication circuit such as a wireless LAN or Bluetooth (registered trademark), and transmits biological data measured by detector 33 to user terminal 2. The biological data is received by communicator 24 of user terminal 2, and transmitted to server 1 via network NT.

Business operator server 4 comprises controller 41, memory 42, and communicator 43. Controller 41 is composed of a processor such as a CPU or a FPGA, and controls the whole of business operator server 4. Memory 42 stores a computer-readable program for allowing a computer to serve as business operator server 4.

Communicator 43 is composed of a communication circuit that connects business operator server 4 to network NT and allows business operator server 4 to communicate with business operator terminal 5. In the present disclosure, communicator 43 particularly receives information related to stress and transmits it to business operator terminal 5.

Business operator terminal 5 comprises controller 51, memory 52, display 53, and communicator 54. Controller 51 is composed of a processor such as a CPU, and controls the whole of business operator terminal 5. Memory 52 stores a computer-readable program for allowing a computer to serve as business operator terminal 5. Display 53 displays various images under control of controller 51. In the present disclosure, display 53 particularly displays information related to stress transmitted from server 1. Communicator 54 is composed of a communication circuit of a wireless LAN or a wired LAN, for example. In the present disclosure, communicator 54 particularly receives information related to stress.

Sequence

Figure 13:
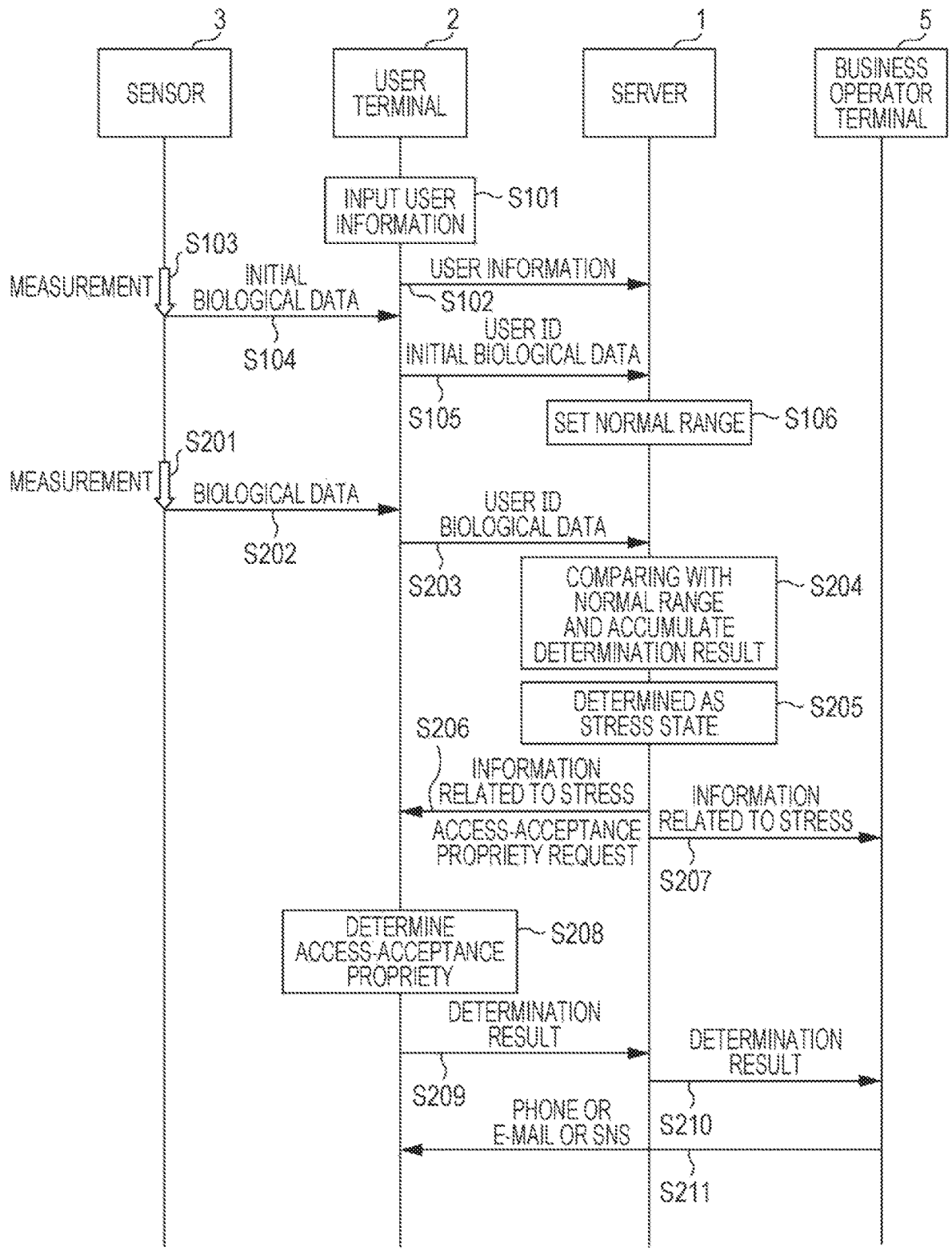
FIG. 13 is a sequence diagram illustrating an example of processing of a biological information system illustrated in FIG. 11.

FIG. 13 is a sequence diagram illustrating an example of processing of a biological information system illustrated in FIG. 11. The sequence diagram is divided into initial phases from S101 to S106 and normal phases after S201. The initial phases are performed to calculate a normal range of a user, and performed immediately after introduction of care service. The normal phases are preformed to monitor a state of stress on a user using the normal range calculated in the initial phases.

The initial phases are performed when a user first starts an application for user terminal 2 to receive care service in user terminal 2, for example.

First, display 23 of user terminal 2 receives input of user information (S101). Display 23 here may display a registration screen for causing the user to input the user information such as a user ID, a telephone number, an e-mail address, an SNS account and the like into the registration screen. As the user ID, a user ID issued when the user made an insurance contract with the insurance company may be used, for example. Alternatively, as the user ID, a user ID issued when server 1 receives the user information in S102 described below may be notified to user terminal 2. In this case, the user is not required to input the user ID into the registration screen.

Next, controller 21 of user terminal 2 causes communicator 24 to transmit the received user information to server 1 (S102). The transmitted user information is stored in user information table T1 by controller 41 of server 1.

Subsequently, detector 33 of sensor 3 measures initial biological data on the user (S103). Next, controller 31 of sensor 3 causes communicator 34 to transmit the measured initial biological data to user terminal 2 (S104).

When communicator 24 receives the initial biological data in user terminal 2, controller 21 transmits the initial biological data to server 1 while associating the initial biological data with the user ID (S105).

The initial biological data is used for calculating a normal range of the user based on the premise that the user is not in a stress state. Then, when the transmission of the user information is finished (S102), user terminal 2 may display a message such as "to measure biological data, wear the sensor and stay quiet for a while", for example, in display 23. Data analyzer 111 of server 1 sets the normal range (S106). The normal range set is stored in normal-range data table T2 by data analyzer 111 of server 1 while being associated with the user ID.

Up to this point, the initial phases are finished. After this, the normal phases are performed.

First, detector 33 measures biological data in sensor 3 (S201), and controller 31 causes communicator 34 to transmit the biological data to user terminal 2 (S202).

Next, when communicator 24 receives the biological data in user terminal 2, controller 21 causes communicator 24 to transmit the biological data to server 1 while associating the biological data with the user ID (S203).

Subsequently, when communicator 13 receives the biological data in server 1, data analyzer 111 compares the biological data with the normal range, and accumulates a determination result (S204). The determination result is accumulated in the "determination result" field of the record of the corresponding user in normal-range data table T2 while the user ID is allowed to serve as a key.

Next, when it is determined that the user is in a stress state (S205), data analyzer 111 transmits information related to stress along with an access-acceptance propriety request to user terminal 2 (S206). Data analyzer 111 also transmits information related to stress to business operator terminal 5 using communicator 13 (S207).

Subsequently, when communicator 24 receives information related to stress in user terminal 2, controller 21 asks the user about access-acceptance propriety using display 23 and receives a determination result from the user (S208). Then, controller 21 may cause display 23 to display an image including a "YES" button for permitting communication from a counseling business operator, and a "NO" button for permitting no communication. When the user selects the "YES" button, controller 21 may determine that the user permits access from the counseling business operator and transmit a determination result of access permission. Meanwhile, when the user selects the "NO" button, controller 21 may determine that the user does not perm it access from the counseling business operator and transmit a determination result of refusing access.

Next, communicator 24 in user terminal 2 transmits the determination result to server 1 (S209). Subsequently, communicator 13 in server 1 receives the determination result, and transmits the determination result to business operator terminal 5 (S210).

Next, when communicator 54 in business operator terminal 5 receives the determination result, the determination result of access permission allows controller 51 to communicate with user terminal 2 of the corresponding user using telephone, e-mail, or SNS (S211). In the case of communication with phone, a staff of a counseling business operator may directly phone the user to tell a message of concerning the user, for example. In the case of communication with e-mail, the staff of the counseling business operator may create an e-mail in which a message of concerning the user is described using business operator terminal 5 and transmit the e-mail to the corresponding e-mail address of the user, for example. In the case of communication with SNS, the staff of the counseling business operator may log on the corresponding SNS site of the user using business operator terminal 5 to transmit a message of concerning the user, for example.

As a message of concerning the user, a message such as "How are you feeling recently?", or "Do you have any worries?" can be used. The user receiving the message replies to the message for the staff. The staff and the user repeat this kind of communication until the user is satisfied to some extent. This enables the user to have a feeling of security such as having the staff listen to an anxiety and a worry through communication with the staff, so that a stress state is relieved.

When it is not determined to be a stress state in S205, processing as S206, S207, S208, S209, S210, and S211 is not performed. While business operator server 4 is used for communication between server 1 and business operator terminal 5, business operator server 4 is not illustrated in FIG. 13. However, this is an example, and server 1 and business operator terminal 5 may directly communicate with each other without using business operator server 4.

Figure 14:
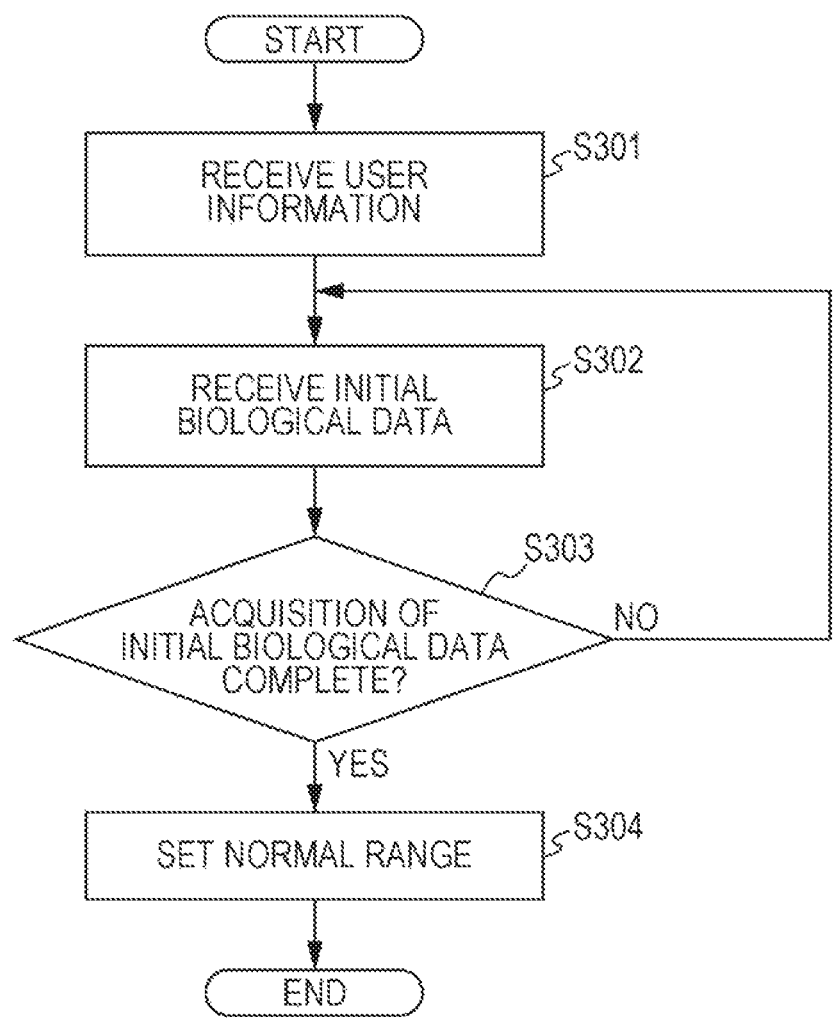
FIG. 14 is a flowchart illustrating detailed processing in an initial phase according to the first embodiment of the present disclosure.

FIG. 14 is a flowchart illustrating detailed processing in an initial phase according to the first embodiment of the present disclosure. This flowchart is performed by server 1. First, communicator 13 receives user information transmitted from user terminal 2 (S301).

Next, communicator 13 receives initial biological data transmitted from user terminal 2 (S302). Subsequently, when the initial biological data has not been acquired (NO in S303), data analyzer 111 returns processing to S302. Meanwhile, when the initial biological data has been acquired (YES in S303), data analyzer 111 allows the processing to proceed to S304. Then, data analyzer 111 may complete acquisition of the initial biological data when the amount of the received initial biological data reaches a predetermined amount enough to calculate a normal range, or when a predetermined measurement period of time elapses after measurement of the initial biological data is started. In the present disclosure, depending on a measurement interval of biological data, one hour, two hours, three hours, one day, two days, three days, or the like is used as a measurement period of time in the initial phases, for example. When a measurement interval of biological data is short, for example, a large amount of initial biological data can be acquired in a short time. Accordingly, a measurement period of time of the initial biological data is shortened. When one hour is used as a measurement interval of biological data, for example, half a day, one day, two days, three days, or the like is used as a measurement period of time of initial biological data, for example. When one minute or one second is used as the measurement interval of biological data, ten minutes, twenty minute, one hour, two hours, three hours, or the like can be used initial biological data can be used as the measurement period of time of initial biological data, for example. However, these numeric values are only an example, and may be appropriately changed.

In the present disclosure, user information is registered in an early stage of pregnancy, so that the measurement period of time of initial biological data corresponds to an example of the predetermined period of time in the early stage of pregnancy of the user. The measurement interval of biological data corresponds to an example of the unit period of time.

Next, data analyzer 111 sets a normal range using the initial biological data acquired (S304). For example, it is assumed that initial biological data as shown in FIG. 6A is acquired. In this case, data analyzer 111 analyzes the initial biological data acquired to extract an upper limit peak and a lower limit peak of biogas concentration. Then, data analyzer 111 may calculate a value as upper limit DH by adding a predetermined margin to the upper limit peak, and a value as lower limit DL by subtracting the predetermined margin from the lower limit peak. Alternatively, data analyzer 111 may calculate a value as upper limit DH by adding a predetermined margin to an average value of upper peaks, and a value as lower limit DL by subtracting the predetermined margin from an average value of lower peaks. As described above, a normal range for each user is set.

Figure 15:
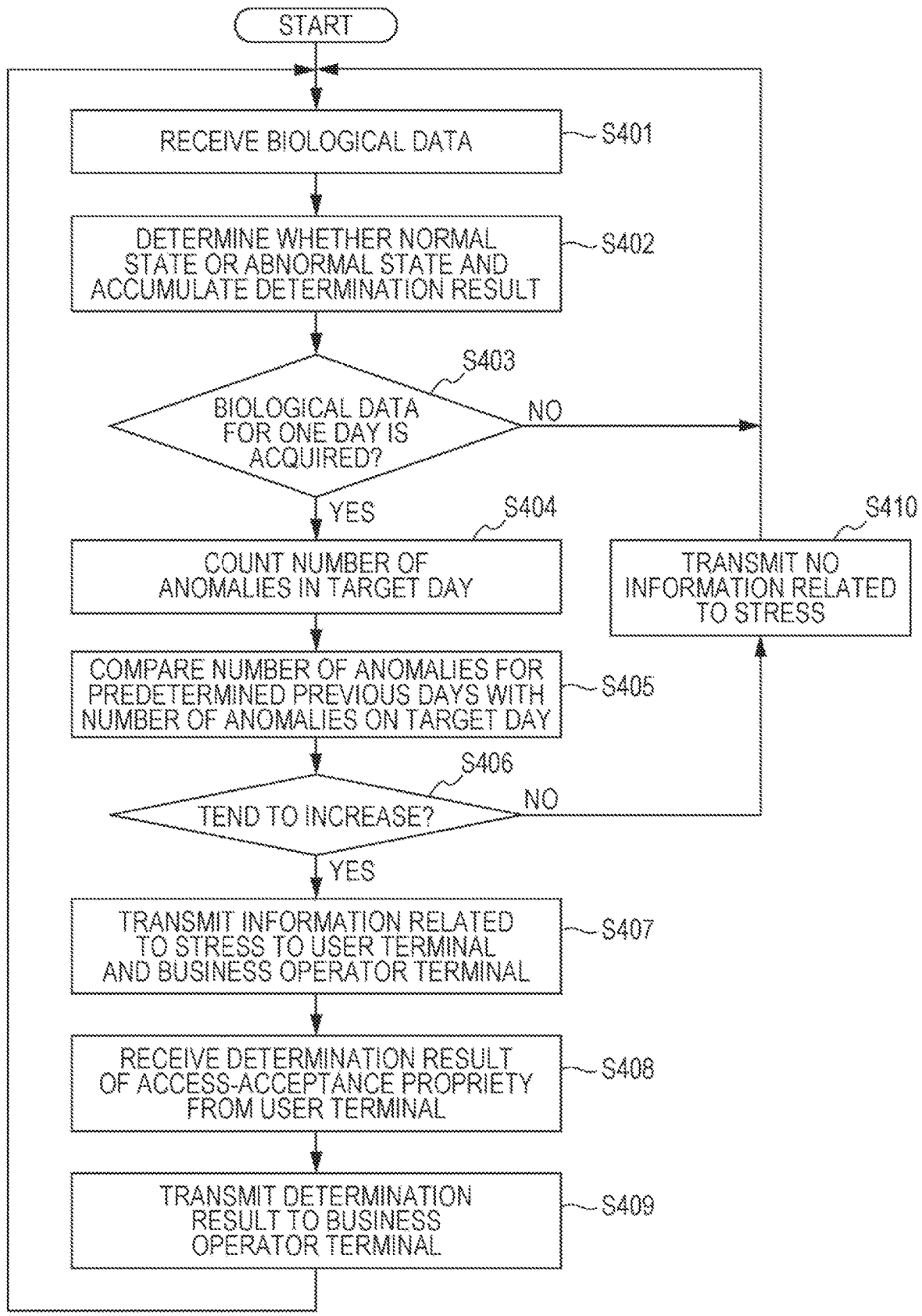
FIG. 15 is a flowchart illustrating detailed processing in a normal phase according to the first embodiment of the present disclosure.

FIG. 15 is a flowchart illustrating detailed processing in the normal phases according to the first embodiment of the present disclosure. The flowchart of FIG. 15 is periodically performed by server 1 at a measurement interval of biological data with sensor 3. In the description below, the case of using one day as the predetermined period of time is exemplified.

First, communicator 13 receives biological data from user terminal 2 (S401). Next, data analyzer 111 compares biogas concentration indicated by the biological data with the normal range of the corresponding user to determine whether a stress state is normal or abnormal, and accumulates a determination result in biological data table T4 (S402). Specifically, data analyzer 111 may store the determination result in biological data table T4 while associating the determination result with a user ID, a measurement date, and a biogas concentration, Refer to Biological data table T4 in FIG. 12. In the record in the first line, "2017.2.15" is described in the "date" field, and "10:00-11:00" is described in the "time" field. This is because the measurement interval of biological data was set at one hour, and the biological data was measured between ten o'clock and eleven o'clock on Feb. 15, 2017.

In the present disclosure, furfural is used as biogas to be measured. Furfural has a negative correlation with a level of stress. Thus, data analyzer 111 may determine that a stress state is abnormal when a biogas concentration is less than lower limit DL of the normal range, and determine that the stress state is normal when the biogas concentration is equal to or more than lower limit DL.

Next, when biological data for one day is acquired (YES in S403), data analyzer 111 allows processing to proceed to S404. When the biological data for one day is not acquired (NO in S403), data analyzer 111 returns the processing to S401, and acquires biological data measured next.

When "0:00" appears in the "time" field, data analyzer 111 may determine YES in S403, and then biological data for one day acquired in the previous day may be treated as biological data on a processing object on a target day.

Next, data analyzer 111 extracts corresponding biological data on the user on the target day from biological data table T4, and counts the number of anomalies in the biological data extracted (S404). Then, data analyzer 111 may count the number of biological data described as "abnormal" in the "determination result" field in the corresponding biological data on the user on the target day in biological data table T4.

Subsequently, data analyzer 111 compares a count value of the number of anomalies on the target day with a count value of the number of anomalies for predetermined previous days to determine whether stress tends to increase (S405). For example, the predetermined previous days are two days. In addition, a count value of the number of anomalies for each day is indicated as E. In this case, data analyzer 111 may determine that stress tends to increase, when the following relationships are satisfied: $\Delta E1=E(\text{target day})-E(\text{the day before})>$a reference differential value; and $\Delta E2=E(\text{the day before})-E(\text{two days before})>$the reference differential value, for example. Meanwhile, data analyzer 111 may determine that stress does not tend to increase, when the following relationship is satisfied: $\Delta E1=E(\text{target day})-E(\text{the day before})\leq$the reference differential value. As the reference differential value, an integer of one or more can be used, for example. Alternatively, an integer of two or more may be used as the reference differential value to disregard an event in which a count value increases due to a measurement error or the like. While two days are exemplified as the predetermined previous days, they are an example, and may be one day or three or more days.

Next, when stress tends to increase (YES in S406), data analyzer 111 transmits information related to stress to user terminal 2 using communicator 13 while associating it with an access-acceptance propriety request, and transmits the information related to stress to business operator terminal 5 (S407), As timing of transmitting the information related to stress, a predetermined time in the next morning (e.g., seven o'clock) may be used, for example.

Meanwhile, when stress does not tend to increase (NO in S406), data analyzer 111 does not transmit the information related to stress (S410), and returns processing to S401.

Next, communicator 13 receives the determination result of access-acceptance propriety from user terminal 2 (S408), Subsequently, communicator 13 transmits the determination result of access-acceptance propriety to business operator terminal 5 (S409). When the processing in S409 is finished, the processing returns to S401.

As described above, it is determined whether a frequency of appearance of stress less than a normal range tends to increase.

Information Related to Stress

As information related to stress, information indicating that stress accumulated in the user requires attention is output from when a user is first determined to be in a stress state to a predetermined number of times. As the information related to stress, information indicating that stress of the user is less than a predetermined normal range is output in a subsequent output after the predetermined number of times. In this way, the information related to stress is changed in severity of notification in a stepwise manner.

Figure 16:
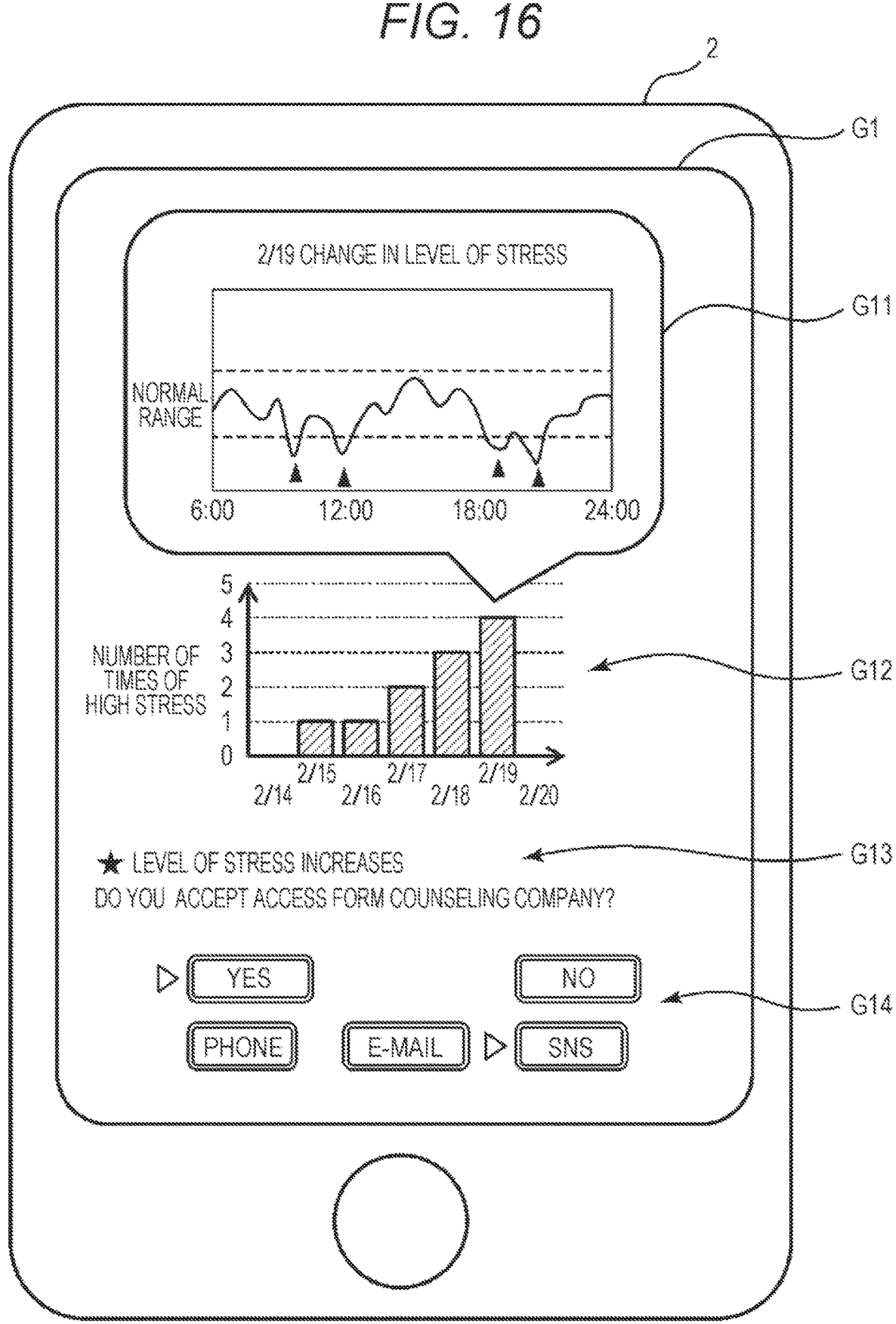
FIG. 16 illustrates an example of a display screen displayed in a user terminal as information related to stress.

FIG. 16 illustrates an example of display screen G1 displayed in user terminal 2 as information related to stress. Display screen G1 includes graph G11, graph G12, message display section G13, and input section G14.

Graph G12 shows a relationship between the number of times of high stress on a target day (here, February 19) and that in predetermined previous days (here, five days from February 14 to February 18). In graph G12, the number of times of high stress indicates the number of times in which biogas concentration is less than a normal range in each day. In the example of graph G12, the number of times of high stress tends to increase from February 16 to February 19, so that it is determined that stress tends to increase, and then display screen G1 is displayed in user terminal 2.

Graph G11 shows temporal transition of level of stress in a predetermined period of time (here, from six o'clock to twenty-four o'clock) in a day when it is determined that stress tends to increase (here, February 19). The level of stress shown in graph G11 corresponds to biogas concentration. In graph G11, a triangular marker is displayed at each place where a level of stress less is than the lower limit of the normal range to enable a user to easily recognize the place where the level of stress is high.

When detecting operation of the user to select a desired day in graph G12, user terminal 2 may display graph G11 of the selected day in display screen G1. This enables the user to find out a cause (stressor) of increase in stress by recalling life of the user itself in the previous days.

Graphs G11 and G12 are each an example of information indicating that stress on a user is less than a predetermined normal range.

Message display section G13 displays a message for notifying a user of a high level of stress. Here, a message, "A level of stress increases", is displayed. Display screen G1 of FIG. 16 shows output from when it is first determined that the user is in a stress state to a predetermined number of times, so that message display section G13 displays the message, "A level of stress increases". The message is an example of information indicating that stress accumulated in the user requires attention. In a subsequent output after the predetermined number of times, message display section G13 displays information indicating that stress of the user is less than the predetermined normal range. In this case, message display section G13 displays a message such as "Be careful because stress is less than the predetermined normal range", for example.

Input section G14 is used to allow the user to input a determination result of access-acceptance propriety. Input section G14 displays a message described as "Do you accept access from the counseling company?", an "YES" button, a "NO" button, a "telephone" button, an "e-mail" button, and an "SNS" button. The counseling company is the counseling business operator.

The "YES" button is selected when the user permits the access-acceptance propriety. The "NO" button is selected when the user does not permit access-acceptance propriety. When the user selects the "YES" button, a triangular cursor is displayed on the left side of the "YES" button. When the user selects the "NO" button, a triangular cursor is displayed on the left side of the "NO" button. This enables the user to easily find out what button is selected.

When the user selects the "YES" button, a determination result of "permission" of the access-acceptance propriety is transmitted to server 1 from user terminal 2. When the user selects the "NO" button, a determination result of "refusal" of the access-acceptance propriety is transmitted to business operator terminal 5 from user terminal 2 via server 1.

The "telephone" button is selected when the user permits access by phone. The "e-mail" button is selected when the user permits access with an e-mail. The "SNS" button is selected when the user permits access with an SNS. When the user selects any one of the "telephone" button, the "e-mail" button, and the "SNS" button, a triangular cursor is displayed on the left side of the selected button. This enables the user to easily find out what button is selected.

When the user selects any one of the "telephone" button, the "e-mail" button, and the "SNS" button, a result of the selection is transmitted to business operator terminal 5 from user terminal 2 via server 1. Thus, a staff of the counseling business operator contacts with the user permitting the access-acceptance propriety using an access method corresponding to the button selected by the user.

While an aspect of allowing a user to select any one of the phone, the e-mail, and the SNS is shown here, the present disclosure is not limited to this, and thus an aspect of allowing the user to select any plurality of the phone, the e-mail, and the SNS may be applied. Input section G14 is an example of display information allowing a user to determine whether to accept access from the counseling business operator.

Figure 17:
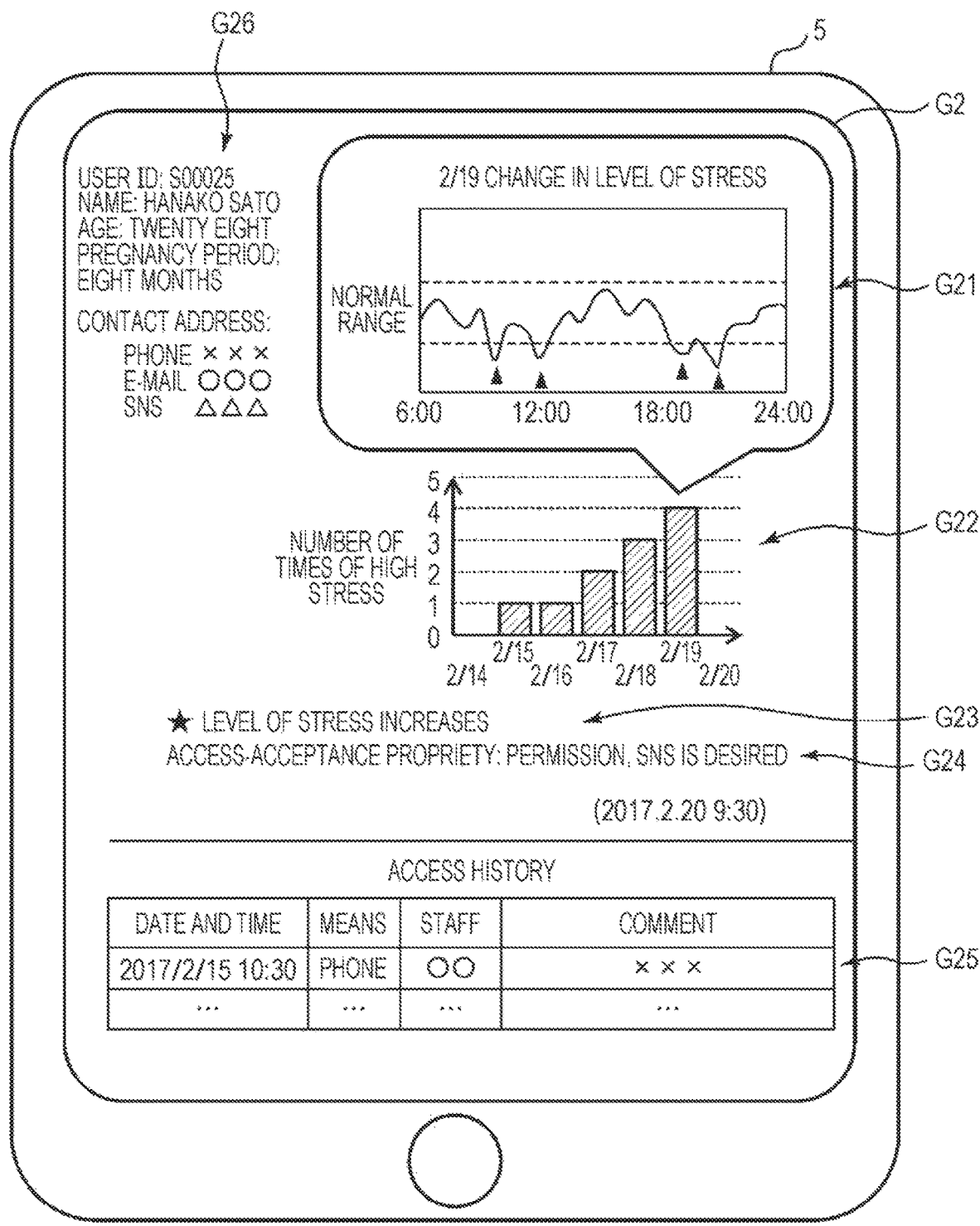
FIG. 17 illustrates an example of a display screen displayed in a business-operator terminal as information related to stress.

FIG. 17 illustrates an example of display screen G2 displayed in a business operator terminal 5 as information related to stress. Display screen G2 includes graph G21, graph G22, message display section G23, access propriety display section G24, access history display section G25, and user information display section G26.

Graph G21, graph G22, and message display section G23 are identical to graph G11, graph G12, and message display section G13 of FIG. 16, respectively.

Access propriety display section G24 displays a determination result of access-acceptance propriety selected by the corresponding user and an access method. Here, the user selects the "permission" as the determination result of the access-acceptance propriety, and the "SNS" as the access method. Thus, access propriety display section G24 displays "access-acceptance propriety: permitted, SNS is desired". This enables a user to determine whether to contact with the corresponding user. In addition, access propriety display section G24 describes "2017.2.20 9:30", so that a time at which the user inputs the determination result of the access-acceptance propriety is also displayed.

Access history display section G25 displays a history of contact with the corresponding user by a staff. In access history display section G25, one contact is assigned to one line, and a "date and time" section, a "means" section, a "staff" section, and a "comment" section are included. The "date and time" section displays a date and time when the staff contacts with the user, the "means" section displays an access method (e.g., phone), the "staff" section displays the name of the staff having contacted with the user, and the "comment" section displays a comment of the staff having contacted with the user. In the "comment" section, the staff describes impression of the user, or the like, for example. For example, in the "comment" section, a content indicating that the user positively replied to a question of the staff.

Access history display section G25 shows an access history that is stored in a database in business operator server 4, for example, and business operator terminal 5 may display the access history using the database.

User information display section G26 displays user information to be accessed. Here, a "user ID", a "name", a "pregnancy period", and a "contact address" are displayed. These kinds of information are stored in a database in server 1, and are managed. The database may be included in user information table T1 illustrated in FIG. 12. In this case, the "name" and the "pregnancy period" may be added in user information table T1 illustrated in FIG. 12.

In the example of FIG. 17, access propriety display section G24 displays "access is permitted, SNS is desired", so that the staff accesses a contact address of the SNS in user information display section G26 using business operator terminal 5 to communicate with the user.

As described above, display screen G2 displays not only user information on a user, to be accessed, but also a changing pattern of level of stress and a tendency of change in the number of times of high stress, so that the staff can smoothly communicate with the user to be contacted while grasping a personality and a level of stress of the user to be contacted.

Schedule Information

Display screens G1 and G2 illustrated in FIGS. 16 and 17, respectively, may display schedule information on a corresponding user. In this case, server 1 may include a database for managing schedule information on a user.

The database for managing the schedule information stores information items such as a "user ID", a "schedule", and a "date", for example, while associating them with each other. The "schedule" is an action schedule (e.g., a "conference", etc.) of a user, and is received by the user with user terminal 2, for example. The "date" is a scheduled date in which the action schedule described in the "schedule" is taken, and is received by the user with user terminal 2.

When transmitting information related to stress, server 1 transmits the information related to stress to user terminal 2 and business operator terminal 5 while including schedule information on the corresponding user for predetermined previous days in the information.

User terminal 2 and business operator terminal 5 may create display screens G1 and G2, respectively, using the schedule information. The schedule information may be displayed in a display mode in which schedule information on a user is displayed in graphs G11 and G21 while being associated with a time period. For example, an aspect of displaying the schedule of the user while the schedule is associated with time indicated in each of graphs G11 and G21 may be used. This enables the user to easily find out a cause and effect relationship between stress and action of the user itself.

As described above, according to the first embodiment, the amount of stress is objectively determined using concentration of furfural having a correlation with the amount of stress, so that a sign of postpartum depression can be objectively determined without being affected by a subjective viewpoint of a pregnant woman. When a frequency of appearance of concentration of furfural less than the normal range tends to increase, information related to stress is transmitted to user terminal 2. This enables a pregnant woman itself to objectively recognize a sign of postpartum depression in a pregnancy period, so that prevention of the postpartum depression can be expected. In this case, the information related to stress is also transmitted to business operator terminal 5, so that a staff also can objectively determine a sign of postpartum depression of the user. Thus, prevention of the postpartum depression can be expected by relieving stress of the user through communication with the user.

Second Embodiment

Figure 18:
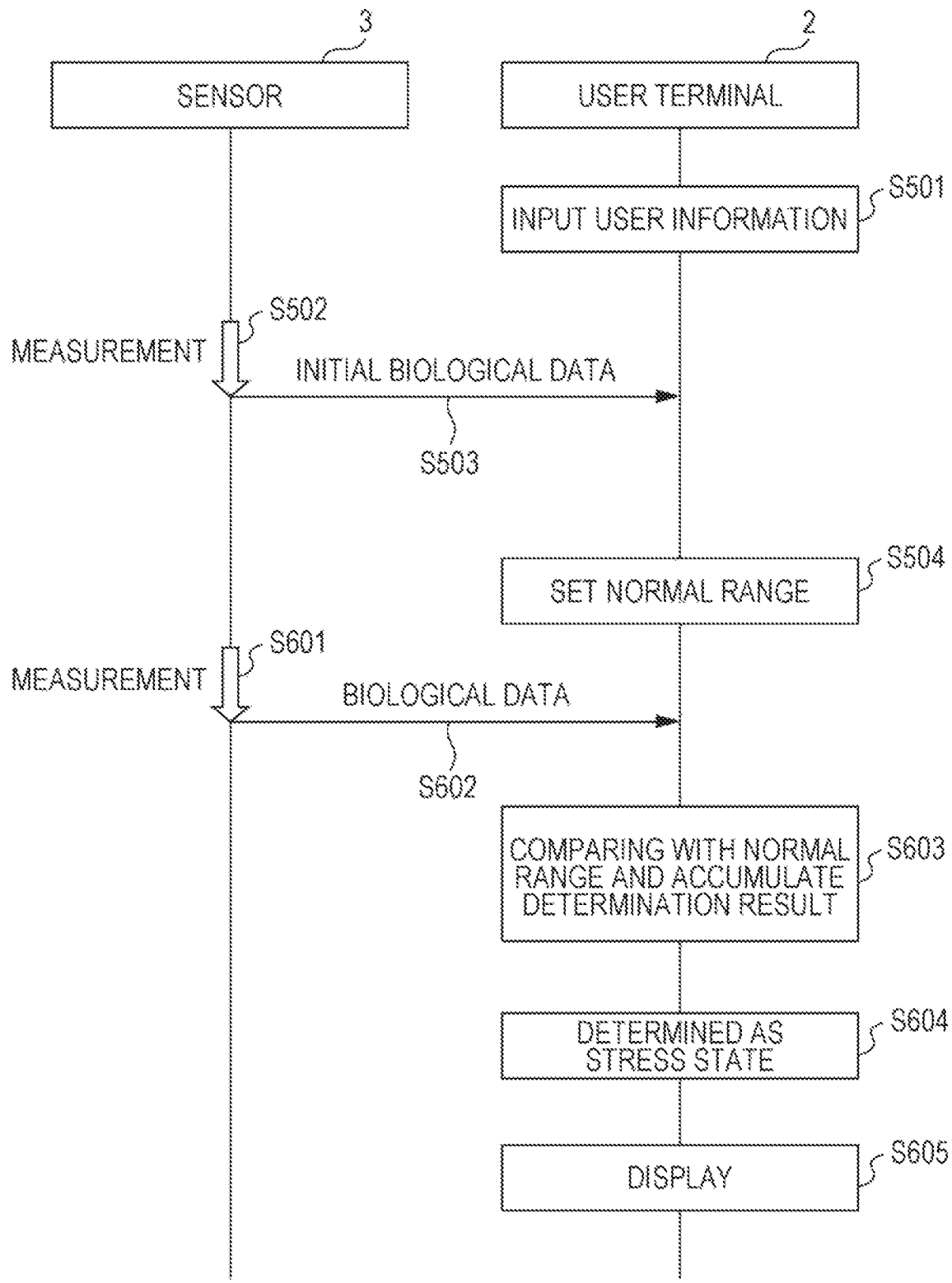
FIG. 18 is a flowchart illustrating detailed processing in a normal phase according to the second embodiment of the present disclosure.

Second embodiment includes user terminal 2 into which functions of server 1 are incorporated. In the second embodiment, the component same as that in the first embodiment is designated by the same reference sign to eliminate duplicated description. FIG. 18 is a sequence diagram illustrating processing of an information processing system according to the second embodiment the present disclosure.

FIG. 18 is different from FIG. 13 in that server 1 and business operator terminal 5 are eliminated and the information processing system includes sensor 3 and user terminal 2. S501 to S504 correspond to the initial phases.

S501, S502, and S503 are identical to S101, S103, and S104, in FIG. 13, respectively. S504 is identical to S106 in FIG. 13 except for a processing subject that is not server 1 but user terminal 2.

S601 to S605 correspond to the normal phases. S601 and S602 are identical to S201 and S202 in FIG. 13, respectively. S603 and S604 are identical to S204 and S205 in FIG. 13, respectively, except for a processing subject that is not server 1 but user terminal 2.

In S605, controller 21 of user terminal 2 causes display 23 to display information related to stress.

In the example of FIG. 18, while S502 is illustrated only once, S502 is performed multiple times to acquire the number of biological data required to calculate a normal range. While S601 is also illustrated only once, S601 is performed multiple times to determine that a frequency of appearance of biogas concentration less than a lower limit of a normal range tends to increase.

As described above, the information processing system according to the second embodiment enables postpartum depression to be prevented as with the first embodiments even in an aspect of incorporating functions of server 1 in user terminal 2.

The present disclosure is allowed to apply modifications below.

(1) While information related to stress is transmitted to user terminal 2 and business operator terminal 5 in the description above, the information may be transmitted to one of user terminal 2 and business operator terminal 5 in the present disclosure.

Figure 19:
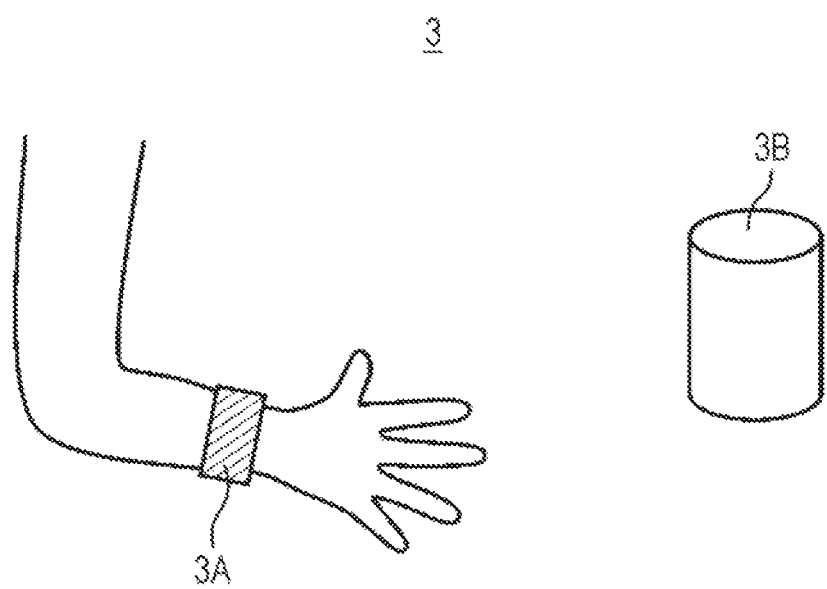
FIG. 19 illustrates an example of sensor 3 according to a modification of the present disclosure.

(2) While sensor 3 is integrally formed in the description above, the present disclosure is not limited to this. FIG. 19 illustrates an example of sensor 3 according to a modification of the present disclosure. Sensor 3 according to the modification includes wearable part 3A to be worn by a user and body part 3B that are separated from each other. Wearable part 3A is composed of a wearable band that is detachable from the wrist of a user. Wearable part 3A is provided with absorbent that absorbs biogas.

Wearable part 3A is configured to be detachable from body part 3B as well. Body part 3B comprises detector 33, controller 31, and communicator 34, illustrated in FIG. 7. When wearable part 3A is worn, body part 3B separates biogas from the absorbent by heating the absorbent with a heater, for example, and analyzes the biogas to extract biogas to be measured (here, furfural), thereby measuring a biogas concentration of the biogas to be measured. Then, body part 3B transmits biological data including the biogas concentration measured to user terminal 2. In the modification, wearable part 3A is reduced in size to enable reduction in burden of a user.

(3) The second embodiment can be applied to a case where a user has an examination by a doctor at a hospital, for example. In this case, a computer of the doctor who examines the user is used as user terminal 2.

In the case, the user visits the hospital at a regular interval (e.g., one week, two weeks, one month; etc.); for example, and is instructed by the doctor to wear sensor 3 for a predetermined period of time (e.g., one day, two days, or three days) just before visiting the hospital. Sensor 3 stores the biological data measured in the predetermined period of time in memory 32 while associating the biological data with measurement time. Memory 32 is here detachable from sensor 3.

The user brings the memory 32 when visiting a hospital. The doctor connects this memory 32 to user terminal 2 to cause user terminal 2 to acquire the biological data acquired in the predetermined period of time. Then, user terminal 2 determines whether a frequency of appearance of biogas concentration less than a normal range tends to increase, and causes display 23 to display information related to stress. Meanwhile, when determining that the frequency does not tend to increase, user terminal 2 does not cause display 23 to display the information related to stress. In this case, user terminal 2 may cause display 23 to display information indicating that stress of the user is normal, for example. This modification enables useful data for preventing postpartum depression to be provided to a doctor who examines a pregnant woman visiting a hospital.

INDUSTRIAL APPLICABILITY

The present disclosure is expected to be capable of preventing postpartum depression, and thus is useful for an information processing system of managing stress on a user.

REFERENCE SIGNS LIST 1 server
2 user terminal
3 sensor
4 business operator server
5 business operator terminal
11 controller
12 memory
13 communicator
21 controller
22 memory
23 display
24 communicator
31 controller
32 memory
33 detector
34 communicator
41 controller
42 memory
43 communicator
51 controller
52 memory
53 display
54 communicator
111 data analyzer
NT network
T1 user information table
T2 normal-range data table
T3 business operator information table
T4 biological data table
U1 user

The invention claimed is:

1. A method for providing information in an information processing system, the method comprising:
acquiring, via a network, biogas information representing a concentration of furfural of a user acquired by a sensor that detects the furfural discharged from a skin surface of the user;
obtaining reference information representing a lower limit of a normal range of the concentration of furfural per unit period of time, using a memory storing the reference information representing the lower limit of the normal range; and
outputting information related to stress of the user to an information terminal after it is determined that a frequency with which the concentration of the furfural of the user per unit period of time is less than the lower limit of the normal range tends to increase, based on the biogas information acquired in a pregnancy period of the user.

2. The method according to claim 1, wherein
the lower limit of the normal range of the concentration of furfural per unit period of time is set for the user as individual information of the user, based on the biogas information acquired in a predetermined period of time in an early stage of the pregnancy period of the user.

3. The method according to claim 1, wherein
the lower limit of the normal range of the concentration of furfural per unit period of time is used commonly to a plurality of users including the user.

4. The method in the information processing system according to claim 1, wherein
when it is not determined that the frequency that the concentration of the furfural of the user per unit period of time is less than the lower limit of the normal range tends to increase, the information related to stress of the user is not output to the information terminal.

5. The method according to claim 1, wherein
the information terminal is a first information terminal of the user.

6. The method according to claim 5, wherein
the information terminal is a second information terminal, of a consulting business operator other than the first information terminal of the user.

7. The method according to claim 1, wherein
the information terminal is a first information terminal of the user, and
the method further includes:
acquiring first address information on the first information terminal and second address information on a consulting business operator from a memory storing the first address information and the second address information, when it is determined that the frequency that the concentration of furfural of the user per the unit period of time is more than the upper limit of the normal range of tends to increase; and
outputting the information related to stress of the user to both of the first information terminal and a second information terminal of the consulting business operator, based on the first address information and the second address information, wherein the second information terminal of the consulting business operator is distinct form the first information terminal.

8. The method according to claim 7, wherein
the information to be output to the first information terminal includes display information for allowing the user to select whether to accept contact of the counseling business operator with the user.

9. The method according to claim 1, wherein
the information related to the stress of the user is used to call the user's attention to a need for reducing stress build up in the user.

10. The method according to claim 1, wherein
the information related to the stress of the user indicates that stress of the user is less than the lower limit of the normal range.

11. The method according to claim 1, wherein
the sensor for detecting furfural is built in a device to be worn by the user.

12. The method according to claim 1, wherein
the information processing system is configured to acquire the biogas information along with a user ID of the user, and to output the information related to stress of the user to the information terminal associated with the user ID of the user.

13. An information processing system comprising:
a server device; and
an information terminal,
wherein the server device is configured to:
 acquire biogas information representing a concentration of furfural of a user acquired by a sensor that detects the furfural discharged from a skin surface of the user;
 obtain reference information representing a lower limit of a normal range of the concentration of furfural per unit period of time, using a memory storing the reference information representing the lower limit of the normal range; and
 output information related to stress of the user to the information terminal after it is determined that a frequency that concentration of furfural of the user per the unit period of time is less than the lower limit of the normal range tends to increase, based on the biogas information acquired in a pregnancy period of the user, and
wherein the information terminal displays the information related to stress of the user on a display of the information terminal.

14. An information terminal comprising:
a display operatively connected to a server device,
wherein the server device is configured to:
 acquire biogas information presenting a concentration of furfural of a user acquired by a sensor that detects furfural discharged from a skin surface of the user,
 obtain reference information representing an upper limit of a normal range of the concentration of furfural per unit period of time, using a memory storing the reference information representing the upper limit of the normal range, and
 output information related to stress of the user to the information terminal after it is determined that a frequency that the concentration of furfural of the user per the unit period of time is more than the upper limit of the normal range tends to increase, based on the biogas information acquired in a pregnancy period of the user, and
wherein the display displays the information related to stress of the user.

15. A method for processing information using a computer, the method comprising:
 acquiring, via a network, biogas information representing a concentration of furfural of a user acquired by a sensor that detects the furfural discharged from a skin surface of the user;
 obtaining reference information representing a lower limit of a normal range of the concentration of furfural per unit period of time, using a memory storing the reference information representing the lower limit of the normal range; and
 outputting information related to stress of the user to display on a display the information related to stress of the user, after it is determined that a frequency that the concentration of the furfural of the user per the unit period of time is less than the lower limit of the normal range tends to increase, based on the biogas information acquired in a pregnancy period of the user.

16. The method according to claim 15, wherein
the display is provided in an information terminal of the user.

17. The method according to claim 15, wherein
the information related to stress of the user is used to call the user's attention to a need for reducing stress build up in the user.

18. The method according to claim 15, wherein
the information related to stress of the user indicates that stress build up in the user is less than the lower limit of the normal range.

* * * * *